(12) United States Patent
Martinez et al.

(10) Patent No.: US 9,481,861 B2
(45) Date of Patent: Nov. 1, 2016

(54) **CULTURE MEDIUM, METHOD FOR CULTURING *SALMONELLA* AND *E. COLI* AND METHOD FOR DETECTING *SALMONELLA* AND *E. COLI***

(75) Inventors: Gabriela Martinez, St. Hyacinthe (CA); Renaud Tremblay, Longueuil (CA); Janikim Larochelle, Beloeil (CA)

(73) Assignee: Foodchek Systems, Inc., Calgary, Alberta (CA)

( * ) Notice: Subject to any disclaimer, the term of this patent is extended or adjusted under 35 U.S.C. 154(b) by 0 days.

(21) Appl. No.: 13/545,594

(22) Filed: Jul. 10, 2012

(65) Prior Publication Data

US 2013/0065240 A1    Mar. 14, 2013

Related U.S. Application Data

(60) Provisional application No. 61/506,937, filed on Jul. 12, 2011.

(51) Int. Cl.
| | |
|---|---|
| *C12N 1/20* | (2006.01) |
| *C12N 1/04* | (2006.01) |
| *C12N 1/00* | (2006.01) |
| *C12Q 1/04* | (2006.01) |
| *C12Q 1/10* | (2006.01) |

(52) U.S. Cl.
CPC ............... *C12N 1/20* (2013.01); *C12Q 1/045* (2013.01); *C12Q 1/10* (2013.01); *C12Q 2304/20* (2013.01)

(58) Field of Classification Search
CPC .................. C12N 1/20; C12Q 1/04
USPC ...................................... 435/252.8
See application file for complete search history.

(56) References Cited

U.S. PATENT DOCUMENTS

| | | | |
|---|---|---|---|
| 5,145,786 A | 9/1992 | Bailey et al. | |
| 5,232,848 A | 8/1993 | Wolfe et al. | |
| 5,296,370 A | 3/1994 | Martin et al. | |
| 5,316,938 A | 5/1994 | Keen et al. | |
| 5,529,920 A | 6/1996 | Cole et al. | |
| 5,536,645 A | 7/1996 | Jay | |
| 5,573,937 A | 11/1996 | Shinmoto et al. | |
| 5,733,572 A | 3/1998 | Unger et al. | |
| 5,871,944 A | 2/1999 | Miller et al. | |
| 6,048,728 A | 4/2000 | Inlow et al. | |
| 6,103,529 A | 8/2000 | Price et al. | |
| 6,136,554 A | 10/2000 | Bochner | |
| 6,153,582 A | 11/2000 | Skelnik | |
| 6,399,381 B1 * | 6/2002 | Blum et al. .................. 435/404 |
| 6,423,540 B2 | 7/2002 | Baur et al. | |
| 6,444,221 B1 | 9/2002 | Shapiro | |
| 6,692,961 B1 | 2/2004 | Judd et al. | |
| 6,733,746 B2 | 5/2004 | Daley et al. | |
| 6,903,134 B2 | 6/2005 | Pflucker et al. | |
| 6,943,021 B2 | 9/2005 | Klausner et al. | |
| 7,018,652 B2 | 3/2006 | Hsia et al. | |
| 7,462,487 B2 * | 12/2008 | Tsao ............... C12N 5/0037 435/253.6 |
| 7,598,083 B2 | 10/2009 | Epstein et al. | |
| RE41,974 E | 11/2010 | Keen et al. | |
| 7,923,245 B2 | 4/2011 | Furue et al. | |
| 8,021,659 B2 | 9/2011 | Naidu et al. | |
| 8,258,125 B2 | 9/2012 | Tunac | |
| 8,349,376 B1 | 1/2013 | Bezzek | |
| 8,377,907 B1 | 2/2013 | Halamicek | |
| 8,377,912 B2 | 2/2013 | Kiliaan et al. | |
| 8,435,547 B2 | 5/2013 | Blass et al. | |
| 8,609,383 B2 | 12/2013 | Young et al. | |
| 8,728,746 B2 | 5/2014 | Rambach | |
| 2002/0012993 A1 * | 1/2002 | Baur et al. .................. 435/371 |
| 2003/0007961 A1 | 1/2003 | Wilburn | |
| 2003/0077564 A1 * | 4/2003 | Brewer ...................... 435/1.1 |
| 2003/0198664 A1 | 10/2003 | Sullivan et al. | |
| 2004/0023374 A1 | 2/2004 | Rappaport et al. | |
| 2005/0013884 A1 | 1/2005 | Rennels | |
| 2005/0208028 A1 | 9/2005 | Brewer | |
| 2007/0141036 A1 | 6/2007 | Gorrochategui Barrueta et al. |
| 2007/0184076 A1 | 8/2007 | Unger et al. | |
| 2008/0019883 A1 * | 1/2008 | Fike et al. .................. 422/139 |
| 2009/0061516 A1 * | 3/2009 | Price et al. ................. 435/383 |
| 2009/0274660 A1 | 11/2009 | Girsh | |
| 2011/0229933 A1 | 9/2011 | Krishnan et al. | |
| 2012/0040014 A1 | 2/2012 | Settineri et al. | |

(Continued)

FOREIGN PATENT DOCUMENTS

| | | |
|---|---|---|
| CA | 2177713 A1 | 6/1995 |
| CA | 2537462 A1 | 3/2005 |
| CN | 1596302 A | 3/2005 |
| JP | 2014-519362 | 2/2016 |
| WO | 96/40861 A1 | 12/1996 |
| WO | 2013/155405 A1 | 10/2013 |

OTHER PUBLICATIONS

Jones et al. 1984 (A Model for the Common Control of Enzymes of Ethanolamine Catabolism in *Escherichia coli*; Journal of General Microbiology; 130:849-860).*

(Continued)

*Primary Examiner* — Gary Nickol
*Assistant Examiner* — Mary Lyons
(74) *Attorney, Agent, or Firm* — Kilpatrick Townsend & Stockton LLP

(57) ABSTRACT

In embodiments there are disclosed culture media, compositions for supplementing culture media, and methods for culturing biological samples. In embodiments the methods are methods for detecting bacteria and in embodiments the bacteria include *Salmonella* spp and in embodiments include *E. coli* spp. In embodiments the media and compositions comprise an alkanolamine and a cobalamin compound.

11 Claims, 2 Drawing Sheets

(56) References Cited

U.S. PATENT DOCUMENTS

| | | |
|---|---|---|
| 2012/0052577 A1 | 3/2012 | Espinosa De Los Monteros et al. |
| 2012/0129727 A1 | 5/2012 | Hossler et al. |
| 2012/0264170 A1 | 10/2012 | Merchant et al. |
| 2012/0282654 A1 | 11/2012 | Yao et al. |
| 2013/0017276 A1 | 1/2013 | Blackman |
| 2013/0040390 A1 | 2/2013 | Pei et al. |
| 2013/0065240 A1 | 3/2013 | Martinez et al. |
| 2013/0230503 A1 | 9/2013 | Homberg et al. |
| 2013/0309768 A1 | 11/2013 | Furue et al. |

OTHER PUBLICATIONS

Roof et al. 1988 (Ethanolamine Utilization in *Salmonella typhimurium*; Journal of Bacteriology, 170(9):3855-3863).*
Brunner, et al., "Serum-free Cell Culture: The Serum-free Media Interactive Online Database," ALTEX, vol. 27(1), pp. 53-62 (2010).
Life Technologies, Technical Resources: 11765—Ham's F-12 Nutrient Mix, 3 pages (2014).
Dehydrated Culture Media, *Salmonella* Rapid Test Elective Medium, Code: CM0857, downloaded from http://www.oxoid.com/UK/blue/prod_detail/prod_detail.asp?pr=CM0857&org=124&c=UK&lang=EN on Oct. 1, 2014, 3 pages.
Dehydrated Culture Media, ONE Broth-*Salmonella*, Code: CM1091, downloaded from http://www.oxoid.com/UK/blue/prod_detail/prod_detail.asp?pr=CM1091&org=124&c=UK&lang=EN on Oct. 1, 2014, 4 pages.
Scarlett, et al., "Microbial Metabolism of Amino Alcohols. Ethanolamine Catabolism Mediated by Coenzyme $B_{12}$-dependent Ethanolamine Ammonia-Lyase in *Escherichia coli* and *Klebsiella aerogenes*," *Journal of General Microbiology*, vol. 95, pp. 173-176 (1976).
Brinsmade, et al., "Minimal Functions and Physiological Conditions Required for Growth of *Salmonella enterica* on Ethanolamine in the Absence of the Metabolosome," *Journal of Bacteriology*, vol. 187, No. 23, pp. 8039-8046 (2005).
Garsin, "Ethanolamine Utilization in Bacterial Pathogens: Roles and Regulation," *Nat Rev Microbiol.*; vol. 8(4),.pp. 290-295. (Apr. 2010).
Gast, et al., "Supplementing Pools of Egg Contents with Broth Culture Media to Improve Rapid Detection of *Salmonella enteritidis,*" *Journal of Food Protection*, vol. 61, No. 1, pp. 107-109 (1998).
Gurtler, et al., "Comparison of supplements* to enhance recovery of heat-injured *Salmonella* from egg albumen," *Letters in Applied Microbiology*, vol. 49, pp. 503-509 (2009).
Jones, et al., "A Model for the Common Control of Enzymes of Ethanolamine Catabolism in *Escherichia coli,*" *Journal of General Microbiology*, vol. 130, pp. 849-860 (1984).
Kofoid, et al., "The 17-Gene Ethanolamine (*eut*) Operon of *Salmonella typhimurium* Encodes Five Homologues of Carboxysome Shell Proteins," *Journal of Bacteriology*, vol. 181, No. 17, pp. 5317-5329 (Sep. 1999).
Lawrence, et al., "Evolution of Coenzyme $B_{12}$ Synthesis Among Enteric Bacteria: Evidence for Loss and Reacquisition of a Multigene Complex," *Genetics*, vol. 142, pp. 11-24 (Jan. 1996).
Penrod, "A pH-Sensitive Function and Phenotype: Evidence that EutH Facilitates Diffusion of Uncharged Ethanolamine in *Salmonella enterica,*" *Journal of Bacteriology*, vol. 186, No. 20, pp. 6885-6890 (Oct. 2004).
Roof, et al., "Ethanolamine Utilization in *Salmonella typhimurium,*" *Journal of Bacteriology*, vol. 170. No. 9, pp. 3855-3863 (Sep. 1988).
Roof, et al., "Functions Required for Vitamin $B_{12}$-Dependent Ethanolamine Utilization in *Salmonella typhimurium,*" *Journal of Bacteriology*, vol. 171, No. 6, pp. 3316-3323 (Jun. 1989).
Taskila, et al., "Modification of Buffered Peptone Water for Improved Recovery of Heat-Injured *Salmonella typhimurium,*" *Journal of Food Science*, vol. 76(3), pp. M157-M162 (2011).

Thiennemitr, et al., "Intestinal inflammation allows *Salmonella* to use ethanolamine to compete with the microbiota," *Proc Natl Acad Sci USA*; vol. 108(42), pp. 17480-17485 (2011).
Chang, G. W., and J. T. Chang. 1975. Evidence for the B12-dependent enzyme ethanolamine deaminase in *Salmonella*. Nature 254:150-151.
Roof, D. M., and J. R. Roth. 1988. Ethanolamine utilization in *Salmonella typhimurium*. J. Bacteriol. 170:3855-3863.
Roof, D. M., and J. R. Roth. 1989. Functions required for vitamin B12- dependent ethanolamine utilization in *Salmonella typhimurium*. J. Bacteriol. 171:3316-3323.
Kofoid, E., C. Rappleye, I. Stojiljkovic, and J. Roth. 1999. The 17-gene ethanolamine (eut) operon of *Salmonella typhimurium* encodes five homologues of carboxysome shell proteins. J. Bacteriol. 181: 5317-5329.
Brinsmade S.R., Paldon T., Escalante-Semerena J.C. 2005. Minimal functions and physiological conditions required for growth of *Salmonella enterica* on ethanolamine in the absence of the metabolosome. J. Bacteriol. 187(23): 8039-46.
Garsin, D.A. 2010. Ethanolamine utilization in bacterial pathogens: role and regulation. Nat. Rev. Microbiol. 8 (4): 290-295.
Chapter 4 entitled Isolation and identification of *Salmonella* from, meat, poultry and eggs products in USDA/FSIS Microbiology Laboratory guidebook, 3rd Edition, Rev. #4, http://www.fsis.usda.gov/PDF/MLG_4_05.pdf.
Chapter 5 entitled *Salmonella* in FDA Bacterial Analytical Manual, 8th Edition, Nov. 2011 Version, http://wvww.fda.gov/Food/ScienceResearch/LaboratoryMethods/BacteriologicalAnalyticalManualBAM/ucm070149.htm.
Chapter 5B entitled Detection and Isolation of non-O157 Shiga-toxin Producing *Escherichia coli* (STEC) from Meat Products in USDA/FSIS Microbiology Laboratory guidebook, 3rd Edition, Rev. #1, http://www.fsis.usda.gov/PDF/Mlg_5B_01.pdf.
Search Report from EP 12811195.2 mailed Feb. 4, 2015.
Brinsmade et al., Minimal Functions and Physiological Conditions Required for Growth of Salmonella enterica on Ethanolamine in the Absence of the Metabolism, *Journal of Bacteriology*, vol. 187, No. 23, Nov. 15, 2005, pp. 8039-8046.
Roof et al., "Functions Required for Vitamin B12-Dependent Ethanolamine Utilization in Salmonella Typhimurium," *Journal of Bacteriology*, vol. 171, No. 6, Jun. 1, 1989, pp. 3316-3323.
Kofoid et al., "The 17-Gene Ethanolamine (eut) Operon of Salmonella Typhimurium Encodes Five Homologues of Carboxysome Shell Proteins," *Journal of Bacteriology*, Sep. 1, 1999, pp. 5317-5329.
Scarlett et al., "Microbial Metabolismof Amino Alcohols, Ethanolamine Catabolism Mediated by Coenzyme 812-Dependent Ethanolamine Ammonia-Lyase in *Escherichia coli*and Klebsiella Aerogenes," *Journal of General Microbiology*, vol. 95, No. 1, Jul. 1, 1976, pp. 173-176.
Jeter, "Cobalamin-Dependent 1,2-Propandiol Utilization by Salmonella Typhimurium," *Journal of General Microbiology*, vol. 136, No. 5, May 1, 1990, pp. 887-896.
Wolf et al., "Isolation and Generic Charachterizations of Bacillus Megaterium Colbamin Biosynthesis-Deficient Mutants," *Journal of Bacteriology*, vol. 166, No. 1, Apr. 1, 1986, pp. 51-58.
Koyuncu et al., "A Comparative Study of Cultural Methods for the Detection of a Salmonella in Feed and Feed Ingredients," BMC Veterinary Research, vol. 5, No. 1, Feb. 3, 2009, p. 6.
De Boer, "Update on Media for Isolation of Eneterobacteriacea from Foods," *International Journal of Food Microbiology*, vol. 45, No. 1, Nov. 1, 1988, pp. 43-53.
Garsin, "Ethanolamine Utilization in Bacterial Pathogens: roles and Regulation," *Nat Rev Microbiol*, vol. 8, No. 4, Apr. 1, 2010, pp. 290-295.
Roth et al., "Cobalmin (Coenzyme B12): Synthesis and Biological Significance," *Annual Review of Microbiology*, vol. 50, 1996, pp. 137-181.

\* cited by examiner

CULTURE MEDIUM, METHOD FOR CULTURING *SALMONELLA* AND *E. COLI* AND METHOD FOR DETECTING *SALMONELLA* AND *E. COLI*

BACKGROUND

1. Field

The subject matter disclosed generally relates to media and methods to culture microorganisms and methods to detect microorganisms.

2. Related Publications
1. Roof, D. M., and J. R. Roth. 1988. Ethanolamine utilization in *Salmonella typhimurium*. J. Bacteriol. 170:3855-3863.
2. Roof, D. M., and J. R. Roth. 1989. Functions required for vitamin B12-dependent ethanolamine utilization in *Salmonella typhimurium*. J. Bacteriol. 171:3316-3323.
3. Chang, G. W., and J. T. Chang. 1975. Evidence for the B12-dependent enzyme ethanolamine deaminase in *Salmonella*. Nature 254:150-151.
4. Garsin, D. A. 2010. Ethanolamine utilization in bacterial pathogens: role and regulation. Nat. Rev. Microbiol. 8 (4): 290-295.
5. Kofoid, E., C. Rappleye, I. Stojiljkovic, and J. Roth. 1999. The 17-gene ethanolamine (eut) operon of *Salmonella typhimurium* encodes five homologues of carboxysome shell proteins. J. Bacteriol. 181: 5317-5329.
6. Brinsmade S. R., Paldon T., Escalante-Semerena J. C. 2005. Minimal functions and physiological conditions required for growth of *salmonella enterica* on ethanolamine in the absence of the metabolosome. J. Bacteriol. 187(23): 8039-46.
7. Chapter 4 entitled Isolation and identification of *Salmonella* from, meat, poultry and eggs products in USDA/FSIS Microbiology Laboratory guidebook, 3rd Edition, Rev. #4, website: fsis.usda.gov/PDF/MLG_4_05.pdf
8. Chapter 5B entitled Detection and Isolation of non-O157 Shiga-toxin Producing *Escherichia coli* (STEC) from Meat Products in USDA/FSIS Microbiology Laboratory guidebook, 3rd Edition, Rev. #1, website: fsis.usda.gov/PDF/Mlg_5B_01.pdf
9. Chapter 5 entitled *Salmonella* in FDA Bacterial Analytical Manual, 8th Edition, November 2011 Version, website: fda.gov/Food/ScienceResearch/LaboratoryMethods/BacteriologicalAnalyticalManualBAM/ucm070149.htm

SUMMARY

In a first embodiment there is disclosed a culture medium comprising biologically effective concentrations of: a cobalamin compound, and an alkanolamine.

In embodiments the cobalamin compound is selected from the group consisting of cobalamin, methyl cobalamin, adenoslycobalamin, hydroxocobalamin and cyanocobalamin.

In embodiments the alkanolamine is ethanolamine.

In embodiments there is disclosed a bacterial culture medium.

In embodiments the bacteria are *salmonella* spp or *E. coli* spp.

In embodiments the bacteria are *salmonella typhimurium*, *E. coli* 157, *Shigatoxin E. coli* or *Enterohemorrhagic E. coli*.

In embodiments the cobalamin compound is present at a concentration of greater than about 0.002M and said alkanolamine is present at a concentration of greater than about 0.001 mg/liter.

In a further series of embodiments there is disclosed a method for culturing a biological sample, the method comprising the step of incubating the sample in the presence of biologically effective concentrations of: a cobalamin compound, and an alkanolamine.

In embodiments the cobalamin compound is selected from the group consisting of cobalamin, methyl cobalamin, adenoslycobalamin, hydroxocobalamin and cyanocobalamin.

In embodiments the alkanolamine is ethanolamine.

In embodiments the method is for culturing bacteria.

In embodiments the bacteria are *salmonella* spp or *E. coli* spp.

In embodiments the bacteria are *salmonella typhimurium*, *E. coli* 157, *Shigatoxin E. coli* or *Enterohemorrhagic E. coli*.

In embodiments the alkanolamine is present at a concentration of greater than about 0.002M and said cobalamin compound is present at a concentration of greater than about 0.001 mg/liter.

The method is for detecting *Salmonella* spp or *E. coli* spp in a sample.

In embodiments the method is for detecting *Salmonella* spp or *E. coli* spp in a sample and the alkanolamine is ethanolamine.

In embodiments the method further comprises a PCR, lectin binding, simple diffusion, lateral diffusion, antibody binding, lateral flow, or flow through step.

In a further series of embodiments there is disclosed a method for preferentially culturing *Salmonella* spp. and *E. coli* spp in a medium, the method comprising supplementing the medium with biologically effective combination of a cobalamin compound and an alkanolamine.

In a further series of embodiments there is disclosed a composition for supplementing a culture medium, the composition comprising: a cobalamin compound, and an alkanolamine.

In embodiments the cobalamin compound is selected from the group consisting of cobalamin, methyl cobalamin, adenoslycobalamin, hydroxocobalamin and cyanocobalamin.

In embodiments the alkanolamine is ethanolamine.

In embodiments the composition is for the growth of bacteria.

In embodiment the bacteria are *salmonella* spp or *E. coli* spp.

In a further series of embodiments there is disclosed a method for detecting *salmonella typhimurium*, *E. coli* 157, *Shigatoxin E. coli* and *Enterohemorrhagic E. coli* in a biological sample, the method comprising culturing the sample in presence of a biologically effective concentration of: ethanolamine; and a cobalamin compound selected from the group consisting of methyl cobalamin, adenoslycobalamin, hydroxocobalamin and cyanocobalamin.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF SELECTED EMBODIMENTS

Terms

Figure 1A:
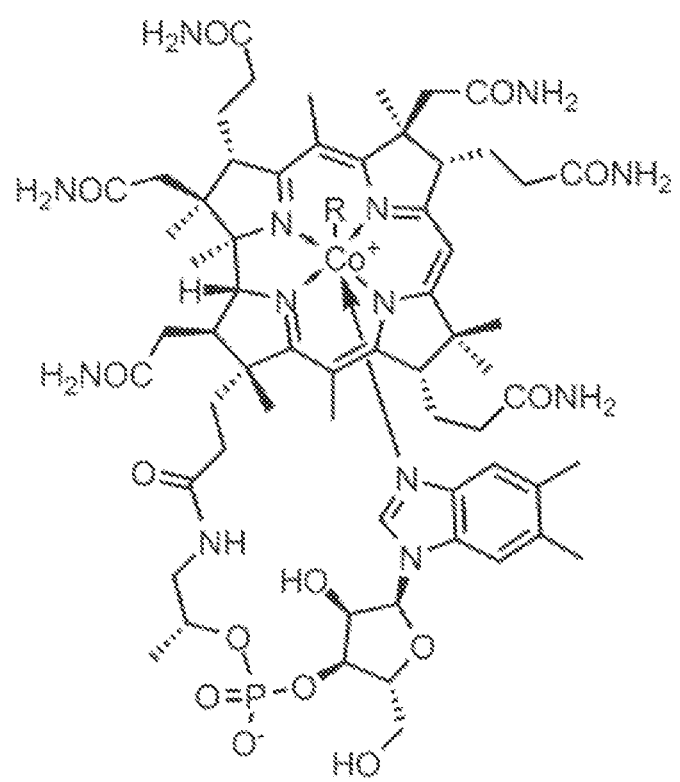
FIG. 1A is the chemical structure of vitamin B12.

In this disclosure, the word "comprising" is used in a non-limiting sense to mean that items following the word are included, but items not specifically mentioned are not excluded. It will be understood that where an embodiments is indicated to comprise a feature or characteristic, it is also contemplated that in alternative variants of the embodiment the embodiment may consist of or may consist essentially of the feature in question. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.).

In this disclosure the singular forms a "an", and "the" include plural referents unless the content clearly dictates otherwise. Thus, for example, reference to a composition containing "a compound" includes a mixture of two or more compounds.

In this disclosure term "or" is generally employed in its sense including "and/or" unless the content clearly dictates otherwise.

In this disclosure, unless otherwise indicated, all numbers expressing quantities or ingredients, measurement of properties and so forth used in the specification and claims are to be understood as being modified in all instances by the term "about". Accordingly, unless indicated to the contrary or necessary in light of the context, the numerical parameters set forth in the disclosure are approximations that can vary depending upon the desired properties sought to be obtained by those skilled in the art utilizing the teachings of the present disclosure and in light of the inaccuracies of measurement and quantification. Without limiting the application of the doctrine of equivalents to the scope of the claims, each numerical parameter should at least be construed in light of the number of reported significant digits and by applying ordinary rounding techniques. Not withstanding that the numerical ranges and parameters setting forth the broad scope of the disclosure are approximations, their numerical values set forth in the specific examples are understood broadly only to the extent that this is consistent with the validity of the disclosure and the distinction of the subject matter disclosed and claimed from the prior art.

In this disclosure the term "media", "medium", "broth", "culture medium", "culture media", "culture broth" and the like all refer to a nutrient mixture suitable to culture a desired microorganism which may be a bacteria or microbe or microorganism or pathogen strain or species. In embodiments media may be or may comprise any core media as defined herein and may be prepared in the form of a powder or concentrate.

In embodiments media contain a pH buffer. In one series of embodiments the pH buffer is a mixture of monobasic and dibasic potassium phosphate but alternative biologically compatible buffers may be suitable such as MOPS (also known as 3-(N-morpholino)propanesulfonic acid, 3-morpholinopropane-1-sulfonic acid; 3-(N-morpholino)propane-sulfonic acid; 3-N-morpholino propansulfonic acid; and 4-Morpholinepropanesulfonic acid), and suitable calcium carbonate buffers, and will be readily selected amongst and implemented by those skilled in the art, to achieve a desired pH for the medium.

In embodiments media may be provided in the form of a powder or concentrate also generally referred to as "powder", "concentrate", "powdered medium", "medium powder", "medium concentrate", "concentrated medium" or the like, comprising a plurality of components and suitable to be combined with a predetermined volume of water to provide a liquid medium with desired concentrations of the particular components. Such a powdered medium or concentrated medium may be complete, meaning that it need only be dissolved in suitable water, normally sterile water, before use. Alternatively in embodiments a powdered or concentrated medium may be partial, meaning that additional components need to be added to provide a complete medium suitable for use. In embodiments a powdered or concentrated medium also includes medium that is at least partly hydrated in concentrated form suitable for dilution to produce the medium for actual use in culturing bacteria. It will be understood that term "medium" or "media" as used herein, unless otherwise required by the context, includes both the final media having components at concentrations suitable for culturing bacteria and microorganisms, and powdered or concentrated media suitable for dilution. The terms "Actero*Salmonella*/STEC" Enrichment Media or "AEM" media and similar terms are used to refer generally to the media according to embodiments.

In this disclosure the terms "Vitamin B12" and "cobalamin" have their normal meaning and both refer to the vitamin having the structural formula shown in FIG. 1A. wherein R represents any group that is compatible with substantially normal Vitamin B12 activity or activity suitable for use in embodiments of the subject matter claimed herein. In particular embodiments and without limiting the foregoing the ligand R coordinated to the central Co2+ ion may be Me, OH, CN, 5'-deoxyadenosyl. For further certainty and without limitation, alternative names for vitamin B12 and biologically active derivatives thereof include: B-12, B12, B Complex Vitamin, Bedumil, Cobalamin, Cobalamine, Cobamin, Cobamine, Complexe Vitaminique B, Cyanocobalamin, Cyanocobalamine, Cyanocobalaminum, Cycobemin, Hydroxocobalamin, Hydroxocobalamine, Hydroxocobalaminum, Hydroxocobemine, Hydroxocobémine, Idrossocobalamina, Methylcobalamin, Methylcobalamine, Vitadurin, Vitadurine, Vitamina B12, Vitamine B12, riboflavin, Vitamin B2; Flavin; Flavine; Lactoflavin; Riboflavine; Vitamin B-2; and Vitamin G.

Similarly the term "cobalamin compound" will be understood to include all substantially biologically equivalent compounds to Vitamin B12 or cobalamin. For example and without limitation those skilled in the art will readily understand that in embodiments reference to Vitamin B12 or cobalamin compounds should be understood to include cyanocobalamin, methyl cobalamin, adenosyl cobalamin, hydroxyl cobalamin and other functionally equivalent chemicals, all of which will be readily identified by those skilled in the art.

Figure 1B:
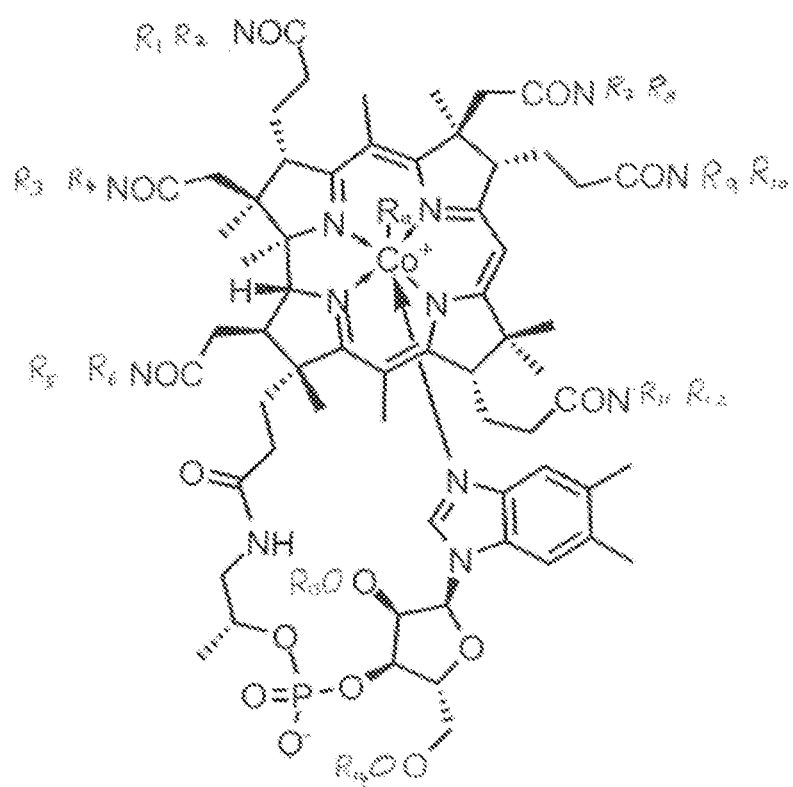
FIG. 1B is the chemical structure of a general cobalamin compound.

It will be further understood that in embodiments a variety of modified or conjugated forms of cobalamin may be biologically effective and all will be readily recognised by those skilled in the art and will be understood to be included in the term "cobalamin compound". In broad aspect, cobalamin compounds may include any compounds of the general structure illustrated in FIG. 1B, wherein R1, R2, R3, R4, R5, R6, R7, R9, R10, R11, R12, R13, R14, R15 may be the same or different from each other, and may independently be H or may be straight or branched chain alkyl, cyclic, cycloalkyl, and may be branched or substituted in a variety of ways all readily apparent to those skilled in the art and may independently comprise, or comprise at least 0, 1, 2, 3, 4, 5, 6, 7, 8 or more carbon atoms. In particular embodiments and without limiting the foregoing the ligand R15 coordinated to the central Co2+ ion may be Me, OH, CN, 5'-deoxyadenosyl.

In this disclosure the term "alkanolamines", also alternately referred to as "amino alcohols" means organic compounds comprising an alcohol group and an amino group on an alkane backbone. Non limiting examples of alkanolamines include methanolamine, ethanolamine, dimethylethanolamine, N-methylethanolamine, heptaminol, isoetarine, norepinephrine, propanolamines, pentanolamines, sphingosine, di-alkanolamines having the formula N(H)R1,R2 and tri-alkylanolamines having the formula NR1,R2,R3. In particular embodiments an alkanolamine may be ethanolamine or may comprise a backbone having 1, 2, 3, 4, 5, 6, 7, 8, 9, 10 or more carbon atoms and may comprise more than one amine group, or more than one hydroxyl group or more than one amine group and more than one hydroxyl group. In embodiments, alkanolamines may be substituted alkanolamines. In particular embodiments an alkanolamine may be ethanolamine. For greater certainty, alternative names for ethanolamine include monoethanolamine, 2-aminoethanol, colamine, Aminoethanol, 2-Hydroxyethylamine, Glycinol, Olamine, Ethylolamine, 2-Amino-1-ethanol. In particular embodiments, alkanolamines are selected from the group consisting of: propylene glycol, monoisopropanol, ethylene glycol, 2-1aminoacetaldehyde, aminopropionitrile, ethylenediamine, 2-aminopropanol, 1,2,diaminopropane, N-methlyaminoethanol, 2-hydroxyethylhydrazine, 3-amino-1-propanol, 2-fluoroethanol, glycolamide, 2-aminoethanol, (R)-(−)1,2,Propanediol.

It will be understood that in this disclosure, unless the context requires otherwise, reference to a medium or solution comprising alkanolamine or cobalamin compounds or to "a" or "an" alkanolamine or cobalamin compound or the like, may include two, three or a plurality of alkanolamines or of cobalamin compounds or of both alkanolamines and cobalamin compounds. Thus by way of example and not limitation the specification that a medium comprises 1 gram per liter of alkanolamine contemplates that the 1 gram may comprise a mixture of different alkanolamines whose weights collectively total 1 gram. Likewise and again by way of example and not limitation a stipulation that a mixture comprises 1 gram of cobalamin compound should be understood to contemplate that the 1 gram comprises portions of one or more cobalamin compounds, for example methylcobalamin, cyanocobalamin and/or other cobalamin compounds, whose collective amounts total 1 gram.

In this disclosure the verb "buffer" means stabilizing the pH of a solution, which may be a culture medium, in a predetermined range, in ways that will be readily apparent to those skilled in the art. The noun "buffer" means a chemical suitable to stabilize the pH of a solution.

In this disclosure the term "base" or "core" medium or broth refers to a partial broth comprising certain basic required components readily recognised by those skilled in the art, and whose detailed composition may be varied while still permitting the growth of the microorganisms to be cultured. Thus in embodiments and without limitation, core medium may comprise salts, buffer, and protein extract, and in embodiments may comprise sodium chloride, monobasic and dibasic sodium phosphate, magnesium sulphate and calcium chloride. In embodiments a liter of core medium may have the general recipe shown in Table 1 but in alternative embodiments core media will or may comprise one or more of water, agar, proteins, amino acids, caesein hydrolysate, salts, lipids, carbohydrates, salts, minerals, and pH buffers and may contain extracts such as meat extract, yeast extract, tryptone, phytone, peptone, and malt extract, and in embodiments medium may be or may comprise luria bertani (LB) medium; low salt LB medium (1% peptone, 0.5% yeast extract, and 0.5% NaCl), SOB medium (2% peptone, 0.5% Yeast extract, 10 mM NaCl, 2.5 mM KCl, 10 mM $MgCl_2$, 10 mM $MgSO_4$), SOC medium (2% peptone, 0.5% Yeast extract, 10 mM NaCl, 2.5 mM KCl, 10 mM $MgCl_2$, 10 mM $MgSO_4$, 20 mM Glucose), Superbroth (3.2% peptone, 2% yeast extract, and 0.5% NaCl), 2×TY medium (1.6% peptone, 1% yeast extract, and 0.5% NaCl), Terrific-Broth (TB) (1.2% peptone, 2.4% yeast extract, 72 mM K2HPO4, 17 mM KH2PO4, and 0.4% glycerol), LB Miller broth or LB Lennox broth (1% peptone, 0.5% yeast extract, and 1% NaCl). It will be understood that in particular embodiments one or more components may be omitted from the core medium. In embodiments media may be simple, complex or defined media and may be enriched media and may be supplemented in a wide variety of ways, all of which will be readily understood by those skilled in the art. In broad aspect those skilled in the art will understand that media contemplates any composition generally suitable for supporting the growth of one or more microorganisms.

TABLE 1

Basic Recipe for Core media according to an embodiment

| Product | Manufacturer (Cat. #) | Qty (g/L) |
|---|---|---|
| Deionised Water | | 1 L |
| Calcium Chloride Dihydrate ($CaCl_2 \cdot 2H_2O$) | BDH Chemicals (M061932) | Between Xg and Yg |
| Potassium Phosphate Monobasic ($KH_2PO_4$) | Sigma (P5655) | Between Xg and Yg |
| Magnesium Sulphate Anhydrous ($MgSO_4$) | BDH Chemicals (BDH0246) | Between Xg and Yg |
| Sodium Chloride (NaCl) | Fisher Scientific (S671) | Between Xg and Yg |
| Bacto TM Yeast Extract | BD Biosciences (212750) | Between Xg and Yg |
| Sodium Phosphate Dibasic ($Na_2HPO_4$) | American Chemicals LTD (7558-79-4) | Between Xg and Yg |
| Sodium Pyruvate ($CH_3COCOONa$) | Sigma (Fluka) 15990 | Between Xg and Yg |

TABLE 1-continued

Basic Recipe for Core media according to an embodiment

| Product | Manufacturer (Cat. #) | Qty (g/L) |
| --- | --- | --- |
| Ferrous sulphate (FeSO$_4$) | Sigma-Aldrich | Between Xg and Yg |
| Citric acid (C$_6$H$_8$O$_7$) | Sigma/Aldrich (251275) | Between Xg and Yg |

In Table 1, X and Y are numerical values expressed in grams. Each of X and Y may independently be 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11.0, 12.0, 13.0, 14.0, 15.0, 16.0, 17.0, 18.0, 19.0 or more than 19.0, or any intervening numbers and in particular embodiments the range X to Y may be delimited by any values of X and Y. It will be understood that in particular embodiments yeast extract may be used in a variety of forms and a range of alternatives to Bacto™ Yeast Extract will be readily selected from by those skilled in the art. By way of example, in particular embodiments, tryptone, meat extracts, and plant extracts may be suitable alternatives, alternative buffers may be used and in some embodiments alternative salts of magnesium, calcium and sodium may be used and in particular embodiments alternatives to magnesium, calcium and sodium may be selected. Those skilled in the art will readily make suitable adjustments to the recipe for base medium to suit particular purposes. It will be understood that any and all variants on the base medium that are compatible with the effectiveness of the enrichment disclosed herein, are intended to be included within the scope of the subject matter claimed.

Table 2 shows the recipe for one possible embodiment of core medium.

Those skilled in the art will readily understand that the growth of a desired microorganism will be best promoted at selected temperatures suited to the microorganism in question. In particular embodiments culturing may be carried out at about 39° C. and the broth to be used may be pre-warmed to this temperature preparatory to inoculation with a sample for testing. In embodiments disclosed herein, culturing may be carried out at any temperature between 33° C. and 43° C. and may be carried out at about 33° C., 34° C., 35° C., 36° C., 37° C., 38° C., or 39° C., or 40° C., or 41° C. or 42° C. or 43° C. or between 33° C. and 34° C., 34° C. and 35° C., 35° C. and 36° C., 36° C. and 37° C., 37° C. and 38° C., 38° C. and 39° C., 39° C. and 40° C., 40° C. and 41° C., 41° C. and 42° C., or 42° C. and 43° C. or at a temperature of between 34° C. and 43° C., or between 35° C. and 42° C., or between 36° C. and 42° C., 38° C. and 42° C. or between 39° C. and 41° C. or between 39° C. and 40° C. or between 38° C. and 39° C., or between 39° C. and 40° C., or between 40° C. and 41° C., or between 41° C. and 42° C. or between 42° C. and 43° C.

In this disclosure "enrichment" or "supplementing" of medium refers to the addition of selected components (also referred to as "supplements" or collectively as a "supplement") to promote the growth, proliferation or other characteristics of one or more desired microorganisms, an "enriched" or "supplemented" medium is a medium that has been so enriched. An "enrichment solution" or "supplement solution" or "supplement" or "additive solution" refers to a solution comprising these additional components. In embodiments the components included in an enrichment solution may comprise a biologically effective combination of alkanolamine and a cobalamin compound and in embodiments the alkanolamine may be ethanolamine and the cobalamin compound may be selected from the group consisting of cobalamin, methyl cobalamin, adenoslycobalamin, hydroxocobalamin and cyanocobalamin. In particular embodiments a supplement may promote or select for the growth of Salmonella spp or E. coli spp. It will be understood that a supplement or enrichment solution may com-

TABLE 2

Core medium according to an embodiment

| Product | Manufacturer (Cat. #) | Qty (g/L) |
| --- | --- | --- |
| Deionised Water | | 1 L |
| Calcium Chloride Dihydrate (CaCl$_2$•2H$_2$O) | BDH Chemicals (M061932) | 0.013 |
| Potassium Phosphate Monobasic (KH$_2$PO$_4$) | Sigma (P5655) | 3 |
| Magnesium Sulphate Anhydrous (MgSO$_4$) | BDH Chemicals (BDH0246) | 0.12 |
| Sodium Chloride (NaCl) | Fisher Scientific (S671) | 0.5 |
| Bacto TM Yeast Extract | BD Biosciences (212750) | 3 |
| Sodium Phosphate Dibasic (Na$_2$HPO$_4$) | American Chemicals LTD (7558-79-4) | 6 |
| Sodium Pyruvate (CH3COCOONa) | Sigma (Fluka) 15990 | 1 g |
| Ferrous sulphate (FeSO$_4$) | Sigma-Aldrich | 0.019 g |
| Citric acid (C$_6$H$_8$O$_7$) | Sigma/Aldrich (251275) | 0.547 g |
| (Total of above ingredients) | | (14.2 g) | prise concentrations of its active ingredients substantially above the final desired concentrations of such ingredients, so that addition of the supplement to the recipient medium may be made without undesirable or excessive change to the volume or concentration of core components of the recipient medium. In embodiments enrichment solutions may comprise about 1 mg/ml cobalamin compound or about 0.125 mg/ml of cobalamin compound or about 16.6M alkanolamine, or may comprise both cobalamin compound and alkanolamine in relative and absolute concentrations such that their addition to a medium is biologically effective to promote the growth of *E. Coli* spp and *Salmonella* spp. In embodiments the alkanolamine may be ethanolamine and the cobalamin compound may be cobalamin.

In embodiments enrichment of media may comprise adding to about one liter of the media about 4 ml of 0.125 mg/ml cobalamin compound solution and about 2 ml of 16.6M alkanolamine solution and in embodiments the alkanolamine may be ethanolamine and the cobalamin compound may be cobalamin. However, it will be readily understood by those skilled in the art that these quantities may be varied to suit particular requirements, and in alternative embodiments the final enriched media may contain about $1\times10^{-6}$, $2\times10^{-6}$, $3\times10^{-6}$, $4\times10^{-6}$, $5\times10^{-6}$, $6\times10^{-6}$, $7\times10^{-6}$, $8\times10^{-6}$, $9\times10^{-6}$, $1\times10^{-5}$, $2\times10^{-5}$, $3\times10^{-5}$, $4\times10^{-5}$, $5\times10^{-5}$, $6\times10^{-5}$, $7\times10^{-5}$, $8\times10^{-5}$, $9\times10^{-5}$, $1\times10^{-4}$, $2\times10^{-4}$, $3\times10^{-4}$, $4\times10^{-4}$, $5\times10^{-4}$, $6\times10^{-4}$, $7\times10^{-4}$, $8\times10^{-4}$, $9\times10^{-4}$, $1\times10^{-3}$, $2\times10^{-3}$, $3\times10^{-3}$, $4\times10^{-3}$, $5\times10^{-3}$, $6\times10^{-3}$, $7\times10^{-3}$, $8\times10^{-3}$, $9\times10^{-3}$, $1\times10^{-2}$, $2\times10^{-2}$, $3\times10^{-2}$, $4\times10^{-2}$, $5\times10^{-2}$, $6\times10^{-2}$, $7\times10^{-2}$, $8\times10^{-2}$, $9\times10^{-2}$, $1\times10^{-1}$, $2\times10^{-1}$, $3\times10^{-1}$, $4\times10^{-1}$, $5\times10^{-1}$, $6\times10^{-1}$, $7\times10^{-1}$, $8\times10^{-1}$, $9\times10^{-1}$, 1, 2, 3, 4, 5, 6, 7, 8, 9, 10, 20, 30, 40, 50, 60, 70, 80, 90, $1\times10^{2}$, $2\times10^{2}$, $3\times10^{2}$, $4\times10^{2}$, $5\times10^{2}$, $6\times10^{2}$, $7\times10^{2}$, $8\times10^{2}$, $9\times10^{2}$, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$, or more than $9\times10^{3}$ g/liter of cobalamin compound and in particular embodiments the cobalamin compound may be in a range whose upper and lower limits are defined by any of the foregoing values and may be about $1\times10^{-3}$ g/liter and in particular embodiments may be between $1\times10^{-4}$ and $1\times10^{-1}$ g/liter, or between $1\times10^{-4}$ and 1 g/liter or may be greater than $1\times10^{-4}$ g/liter, $1\times10^{-3}$ g/liter, $1\times10^{-2}$ g/liter or $1\times10^{-1}$ g/liter. Similarly it will be readily understood by those skilled in the art that the concentration of alkanolamine in the enriched media may approximate or exceed 0.02M alkanolamine, but in particular embodiments the enriched media may contain at least or more than about $1\times10^{-6}$, $2\times10^{-6}$, $3\times10^{-6}$, $4\times10^{-6}$, $5\times10^{-6}$, $6\times10^{-6}$, $7\times10^{-6}$, $8\times10^{-6}$, $9\times10^{-6}$, $1\times10^{-5}$, $2\times10^{-5}$, $3\times10^{-5}$, $4\times10^{-5}$, $5\times10^{-5}$, $6\times10^{-5}$, $7\times10^{-5}$, $8\times10^{-5}$, $9\times10^{-5}$, $1\times10^{-4}$, $2\times10^{-4}$, $3\times10^{-4}$, $4\times10^{-4}$, $5\times10^{-4}$, $6\times10^{-4}$, $7\times10^{-4}$, $8\times10^{-4}$, $9\times10^{-4}$, $1\times10^{-3}$, $2\times10^{-3}$, $3\times10^{-3}$, $4\times10^{-3}$, $5\times10^{-3}$, $6\times10^{-3}$, $7\times10^{-3}$, $8\times10^{-3}$, $9\times10^{-3}$, $1\times10^{-2}$, $2\times10^{-2}$, $3\times10^{-2}$, $4\times10^{-2}$, $5\times10^{-2}$, $6\times10^{-2}$, $7\times10^{-2}$, $8\times10^{-2}$, $9\times10^{-2}$, $1\times10^{-1}$, $2\times10^{-1}$, $3\times10^{-1}$, $4\times10^{-1}$, $5\times10^{-1}$, $6\times10^{-1}$, $7\times10^{-1}$, $8\times10^{-1}$, $9\times10^{-1}$, 1, 2, 3, 4, 5, 6, 7, 8, 9, 10, 20, 30, 40, 50, 60, 70, 80, 90, $1\times10^{2}$, $2\times10^{2}$, $3\times10^{2}$, $4\times10^{2}$, $5\times10^{2}$, $6\times10^{2}$, $7\times10^{2}$, $8\times10^{2}$, $9\times10^{2}$, $1\times10^{3}$, $2\times10^{3}$, $3\times10^{3}$, $4\times10^{3}$, $5\times10^{3}$, $6\times10^{3}$, $7\times10^{3}$, $8\times10^{3}$, $9\times10^{3}$ ethanolamine or a biologically effective precursor or modified form thereof and in particular embodiments may contain between $2\times10^{-3}$ and $2\times10^{-1}$M alkanolamine, and in embodiments may contain between $2\times10^{-3}$ and 2M alkanolamine and in embodiments the alkanolamine may be or may comprise ethanolamine. In particular embodiments of an enriched broth according to embodiments, the alkanolamine may be at a concentration of greater than about 0.001 M, 0.002M, 0.01 M, 0.02M, 0.1 M or 0.2M and the cobalamin compound may be at a concentration of greater than about 0.001 mg/ml, 0.01 mg/ml or 0.1 mg/ml.

In this disclosure "culture conditions" means the parameters for the culturing of a microorganism, and includes the chemical composition and physical properties of the culture medium as well as the temperature, agitation, containment, and duration of the culture and any other parameters that may effect the growth of the microorganism. Thus in particular embodiments, a culture may be maintained at any temperature out at any temperature between 33° C. and 43° C. and may be carried out at about 33° C., 34° C., 35° C., 36° C., 37° C., 38° C., 39° C., 40° C., 41° C., 42° C. or 43° C. or between 33° C. and 34° C., 34° C. and 35° C., 35° C. and 36° C., 36° C. and 37° C., 37° C. and 38° C., 38° C. and 39° C., 39° C. and 40° C., 40° C. and 41° C., 41° C. and 42° C., or 42° C. and 43° C. or at a temperature of between 34° C. and 43° C., or between 35° C. and 42° C., or between 36° C. and 42° C., 38° C. and 42° C. or between 39° C. and 41° C. or between 39° C. and 40° C. or between 38° C. and 39° C., or between 39° C. and 40° C., or between 40° C. and 41° C., or between 41° C. and 42° C. or between 42° C. and 43° C. or between or at any other temperature range compatible with the growth of the bacteria of interest. In particular embodiments the culture temperature may be about 39° C. It will be understood that temperatures above 43° C. and below 33° C. may also be used to culture microorganisms using the media disclosed herein, however it has been found that where it is desired to culture *E. coli* spp or *Salmonella* spp, temperatures outside the range between 43° C. and 33° C. may allow relatively faster growth of other non-desired microorganisms or be less effective in promoting the growth of the microorganism of interest. The pH of culture medium is generally set at between 7 and 8 and for example in particular embodiments is or is about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0 or may be in ranges delimited by any two of the foregoing values. Thus in particular embodiments the pH of culture medium is in ranges with lower limits of 7.0, 7.1, 7.2, 7.3, 7.4, 7.5, 7.6, 7.7, 7.8, or 7.9 and with upper limits of 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0. In one embodiment the medium has a pH between 7.8 and 8.4, in another embodiment the medium has a pH between 7.9 and 8.3 and in yet a further embodiment the medium has a pH between 8.0 and 8.2.

It will be understood that a pH outside of the range pH7-9 may still be useable in embodiments, but that the efficiency and selectivity of the culture may be adversely affected. A culture may be grown for any desired period following inoculation with a sample but it has been found that in embodiments a 7 hour culture period is sufficient to enrich the content of *salmonella* spp or *E. coli* spp sufficiently to permit testing by normal methods. However, in alternative embodiments for particular purposes the culture period will be longer or shorter and will be up to or less than 1, 2, 3, 4, 5, 6, 7, 8, 9, 10, 11, 12, 13, 14 or more hours. Those skilled in the art will readily select a suitable culture period to satisfy particular requirements.

In this disclosure a "microorganism" means a bacterium, which may be a pathogenic bacterium and in embodiments is *Salmonella* spp or *E. Coli* spp. In particular embodiments the *Salmonella* is *salmonella typhimurium*, and the *E. Coli* is *E. Coli* 157, *Shigatoxin E. Coli* (STEC) or *Enterohemoragic E. Coli* (EHEC).

In this disclosure "detecting" a microorganism, means any process of observing the presence or absence of a microorganism, or a change in the presence of a microorganism, in a biological sample, whether or not the microorganism or the change in the microorganism is actually detected. In other words, the act of testing a sample for a microorganism or a change in the level of a microorganism, is a "detection" even if the microorganism is determined to be not present or below the level of sensitivity. Detection may be a quantitative, semi-quantitative or non-quantitative observation and may be based on a comparison with one or more control samples. Detection may be applied to any sample wherein the presence or absence of the microorganism is to be assessed, and in particular embodiments but without limiting the generality of the foregoing, a sample is or comprises any form of biological material and may comprise ground, or unground, meat, poultry, fish, seafood, vegetables, fruit, dairy produce, milk, eggs, packaged food, canned food, bottled food, or wrapped food, or swipe pads or wipes. It will be understood that a variety of detection methodologies are possible and these will be readily selected amongst and implemented by those skilled in the art. In particular embodiments detecting is carried out using PCR, real time PCR, lectins, simple diffusion, lateral diffusion, immunological detection, lateral flow, or flow through methods and such methods include EIA- and ELISA-based assays and may involve incorporating fluorescent or colorimetric detection, may include immunochromatographic technology, and may incorporate molecular techniques such as DNA hybridisation and PCR-based assays. In embodiments detection is carried out using FoodChek™'s MICT™ testing methodology and apparatus wherein an aliquot of the enriched culture is heated to kill the target analyte. The heated sample is loaded in a lateral flow cassette, which is composed of a sample/conjugate pad containing nano-sized magnetic particles conjugated to an antibody that will bind the pathogen's antigen. The tests also contain a second antibody in a narrow strip called the capture zone. Capillary flow takes the loaded liquid through the sample pad to the conjugate pad, where the target bacteria bind to the antibody-coated particles. This immune complex flows into the test strip to the capture zone. The result is an accumulation of magnetic particles in the capture zone. If the target pathogen is absent, immune complexes do not form, particles do not accumulate at the capture line, and the test result is negative. Further downstream, a control line that has been stripped in similar fashion but with a different reagent verifies that the test was performed correctly and that the reagents are still active. The cassette is read in an instrument capable of detecting low concentrations of magnetic particles. The detector senses small changes in a magnetic field along the test strip as it passes under a group of sensing coils. The coils are wound in alternating directions so that a characteristic signal profile is generated by the presence of magnetic particles bound to test or control lines. The instrument compares the detection signal with a positive threshold value encoded in the bar code stuck on each individual cassette, and then reports a positive or negative result. The results are displayed on the instrument's liquid crystal display screen and printed, or transferred to a related computer. In addition to all analysis parameters, the bar code also encodes the test name, lot number, and expiration date, which are printed along with the test result. It will be understood that a variety of recognised testing procedures for *Salmonella* spp, *E. coli* spp and other microorganisms are widely known to those skilled in the art and that such persons skilled in the art will readily combine suitable such detecting methods with the cultures and culture methods disclosed herein. By way of illustration and not limitation, in particular embodiments possible detecting methods include or use the subject matter disclosed in any of U.S. Pat. No. 6,483,303; U.S. Pat. No. 6,597,176; U.S. Pat. No. 6,607,922; U.S. Pat. No. 6,927,570; U.S. Pat. No. 7,323,139, the disclosures of which are hereby incorporated herein by reference in their entirety and further explain the FoodChek™ MICT™ testing methodology which may be optionally used in or with embodiments hereof.

In this disclosure the term "biologically effective" means a compound, chemical or mixture or combination of compounds or chemicals having the desired biological effect. Thus reference to a biologically effective mixture or combination of an alkanolamine and a cobalamin compound means that the mixture has the desired effect of preferentially promoting the growth of the desired microorganism, and in embodiments the microorganism may be one or more of an *E. coli* spp. or a *salmonella* spp.

In this disclosure the term "concentrated" where used with reference to one or more chemicals or components, means a preparation containing a chemical or components or mixture of chemicals or components at concentrations significantly higher than their desirable working concentrations. Thus for example, if it is desired to use a chemical at a concentration of 0.02 M, then a suitable concentrated solution of the chemical may be a 20M solution, so that adding the concentrated solution to, for example, a culture medium, can achieve the desired working concentration without otherwise materially altering the concentration of other components of the culture medium.

In this disclosure the terms "preferentially promoting the growth of" a specified microorganism, and "preferentially culturing" a specified microorganism and like terms, are used with reference to culture conditions which promote or support the growth of the specified microorganism in preference to the growth of other microorganisms. Thus in embodiments methods and media are disclosed which result in increased growth and division of *salmonella* spp. and *E. coli* spp., in preference to other microorganisms. Thus the terms indicate conditions wherein the growth of the specified microorganism is enhanced relative to other microorganisms in a sample, so that growth of the other microorganisms may be inhibited, or may be increased, but that in either case the proportion of the desired, promoted microorganism will rise relative to other microorganisms in the culture. In embodiments the growth in a culture may be exclusively or substantially exclusively the growth of the microorganism of interest.

In this disclosure the terms "sample" and "biological sample" have the same and broadest possible meaning consistent with their context and refer generally and without limitation to anything desired to be tested for the presence of one or more microorganisms of interest, and include all such subject matter whether or not it actually contains any microorganisms, or any microorganisms of interest and whether or not it contains *salmonella* spp. or *E. coli* spp. In embodiments a sample may be obtained by taking a piece or portion, or by use of a swab, wipe, filter, smear, or any other suitable method, all of which will be readily understood and implemented and selected among by those skilled in the art. In particular embodiments a sample is or comprises food material or is or comprises plant or animal material or is or comprises meat, seafood, fish, vegetables, fruit, salads, premade meals, eggs, dairy produce, combined and uncombined food materials, canned goods, or any other form of fresh, raw, cooked, uncooked, frozen, refrigerated, ground, chopped, canned, packaged, heat treated, dried, preserved, refined, or preserved foodstuffs whatsoever. In further embodiments a sample may be taken from an environment, surface, container or location wherein it is desired to determine whether a microorganism of interest is present, for example and without limitation kitchen surfaces, cooking surfaces, food storage containers, eating utensils, refrigerators, freezers, display containers, wrapping materials, live plants and animals and any other environment, location, surface, or material whatsoever that may be of interest to a user. Those skilled in the art will understand and implement suitable methods for selecting, obtaining and handling any sample for use in embodiments. In selected embodiments samples are samples of meat, fish, seafood, vegetables, eggs or dairy produce.

Culture Medium of an Embodiment

In an embodiment there is disclosed a culture medium comprising biologically effective concentrations of: a cobalamin compound, and an alkanolamine. In variants of the embodiment and without limiting other variants of the embodiment, the cobalamin compound is selected from the group consisting of cobalamin, methyl cobalamin, adenosly-cobalamin, hydroxocobalamin and cyanocobalamin In particular variants of the embodiment the alkanolamine is ethanolamine. In embodiments the culture medium is a bacterial culture medium and in embodiments the bacteria are or include *salmonella* spp and *E. coli* spp. or either of the foregoing. In particular variants of the embodiment the bacteria are or may include *salmonella typhimurium, E. coli 157, Shigatoxin E. coli* or *Enterohemorrhagic E. coli*.

In particular variants of the embodiment, the cobalamin compound is present at a concentration of greater than 0.002M and the alkanolamine is present at a concentration of greater than 0.001 mg/liter In one series of variants the *E. coli* is *E. coli* 157 and the *Salmonella* is *Salmonella typhimurium* and in an embodiment the biological sample is a food sample, which may be a meat sample and may be a ground meat sample.

Example of the Embodiment

The composition and use of a non-limiting example of the composition and use of an example of a medium according to the embodiment is as follows.

To prepare the medium, suspend 14.2 g of powdered core medium constituents in 1 liter of distilled water. The composition of core medium according to the example is shown in Table 3. Dispense into a final container and sterilize by autoclaving at 121° C. for 15 minutes. Cool to room temperature. Prior to use, add 2 mL per liter of ethanolamine solution (supplement 1) and 0.5 mL per liter of vitamin B12 (supplement 2). Mix well. These supplements are further illustrated in Table 4. The pH of the medium is between 7.9 and 8.5, with a target value of about 8.2.

It will be understood that while manufacturer information for the components is provided, this is by way of example only, and not by way of limitation. Those skilled in the art will readily understand that the same or equivalent materials or suitable grades may be obtained from a range of alternative sources and those skilled in the art will readily determine suitable alternatives to the components listed in Table 3.

TABLE 3

Composition of a Core Medium according to the embodiment

| Product | Manufacturer (Cat. #) | Qty (g/L) |
|---|---|---|
| Deionised Water | | 1 L |
| Calcium Chloride Dihydrate ($CaCl_2 \cdot 2H_2O$) | BDH Chemicals (M061932) | 0.013 |
| Potassium Phosphate Monobasic ($KH_2PO_4$) | Sigma (P5655) | 3 |
| Magnesium Sulphate Anhydrous ($MgSO_4$) | BDH Chemicals (BDH0246) | 0.12 |
| Sodium Chloride (NaCl) | Fisher Scientific (S671) | 0.5 |
| Bacto TM Yeast Extract | BD Biosciences (212750) | 3 |

TABLE 3-continued

Composition of a Core Medium according to the embodiment

| Product | Manufacturer (Cat. #) | Qty (g/L) |
|---|---|---|
| Sodium Phosphate Dibasic ($Na_2HPO_4$) | American Chemicals LTD (7558-79-4) | 6 |
| Sodium Pyruvate (CH3COCOONa) | Sigma (Fluka) 15990 | 1 g |
| Ferrous sulphate ($FeSO_4$) | Sigma-Aldrich | 0.019 g |
| Citric acid ($C_6H_8O_7$) | Sigma/Aldrich (251275) | 0.547 g |
| (Total of above ingredients) | | (14.2 g) |

TABLE 4

Supplements added to Core Medium to form final medium for use

| Product | Manufacturer (Cat. #) | Qty (mL) |
|---|---|---|
| Ethanolamine (solution) 16.6M (supplement 1) | Sigma (E0135) | 2 |
| Vitamin B12 solution 1 mg/ml (Supplement 2) | Sigma (V6629) | 0.5 |

For Quality Control

Performance: Test 10 mL per liter of medium prepared by inoculating with *S. Typhimurium* ATCC 14028 and *E. coli* O157:H7 ATCC 43895. Both should grow in the medium after a suitable incubation period. The negative control is to incubate the same medium for the same or a longer time period without any inoculant. There should be no bacterial or microorganism growth evident.

When the foregoing mixture (also referred to as "base" or "core" broth or "medium") has cooled, a composition for enriching or supplementing the core broth is added, the composition comprising ethanolamine and Vitamin B12. In practice the ethanolamine and Vitamin B12 may be added to the medium just before use. It will be understood by those skilled in the art that the vitamin solution and ethanolamine should be sterilised before use. In an embodiment the vitamin B12 solution is prepared by mixing 1 mg of vitamin B12 per ml of water (1 mg/mL) and the concentrated ethanolamine and vitamin B12 solution are filter-sterilized prior to use.

Those skilled in the art will also readily understand that for convenience, the base broth or the complete broth may be prepared as a concentrate and diluted with sterile water when desired for use.

In embodiments a biological sample is then added to a desired volume of enriched medium and maintained at a desired temperature for a desired period. Where the microorganism to be detected is *Salmonella* spp, then in an example of the embodiment temperature of the culture medium is between about 38° C. and 40° C. and in further variant of is about 39° C. In embodiments the culture is maintained at the desired temperature, with any desired or necessary agitation, for any desired time period. Where the purpose of the culture is the detection of the microorganism of interest, then a culture duration of about seven (7) hours or more may be adequate for most testing procedures but in particular variant embodiments time periods of at least 1, 2, 3, 4, 5, 6, 7, 8, 9, 10 or more hours will be chosen. However, those skilled in the art will readily adjust the duration, agitation, and temperature of the culture conditions as may be necessary or desirable for particular purposes.

Culture Methods According to an Embodiment

In a further embodiment there is disclosed a method for culturing a biological sample, the method comprising the step of incubating the sample in the presence of biologically effective concentrations of: a cobalamin compound, and an alkanolamine. In variants of the embodiment, the medium is the medium according to a culture medium embodiment. In particular embodiments, the cobalamin compound is selected from the group consisting of cobalamin, methyl cobalamin, adenoslycobalamin, hydroxocobalamin and cyanocobalamin; and in embodiments the alkanolamine is ethanolamine. The method according to the embodiment may be a method for culturing bacteria. In variants of the embodiment the bacteria are *salmonella* spp or *E. coli* spp or include both *salmonella* spp and *E. coli* spp. In variants of the embodiment the bacteria include *salmonella typhimurium, E. coli* 157, *Shigatoxin E. coli* or *Enterohemorrhagic E. coli*. In variants of the embodiment the alkanolamine may be present at a concentration of greater than 0.002M, 0.02M, or 0.2M and the cobalamin compound may be present at a concentration of greater than 0.001 g/liter, 0.01 g/liter or 0.1 g/liter. In embodiments the method is for detecting *Salmonella* spp or *E. coli* spp or both in a biological sample.

In embodiments the method comprises a PCR, lectin binding, simple diffusion, lateral diffusion, antibody binding, lateral flow, or flow through step.

In further embodiments the method is a method for preferentially culturing *Salmonella* spp. and *E. coli* spp in a medium, the method comprising supplementing the medium with biologically effective concentrations of a cobalamin compound and an alkanolamine.

Media Supplements According to an Embodiment

In a further series of embodiments there are disclosed compositions for supplementing a culture medium. In embodiments such a composition comprises a cobalamin compound, and an alkanolamine. In variants of the embodiment and without limitation, the cobalamin compound is selected from the group consisting of cobalamin, methyl cobalamin, adenoslycobalamin, hydroxocobalamin and cyanocobalamin. In embodiments the alkanolamine is ethanolamine. In embodiments the compositions are for the growth of bacteria. In embodiments the bacteria are or include *salmonella* spp or *E. coli* spp and in embodiments are *salmonella typhimurium, E. coli* 157, *Shigatoxin E. coli* and *Enterohemorrhagic E. coli*.

Methods for Detecting Bacteria According to an Embodiment

In an further embodiment there are disclosed methods for detecting bacteria in a biological sample. In embodiments and without limiting other embodiments, the bacteria are or include either or both of *E. coli* spp. and *salmonella* spp. In particular variants of the embodiment the method comprises culturing the sample in presence of a biologically effective combination of: ethanolamine and a cobalamin compound. In embodiments the cobalamin compound is selected from the group consisting of methyl cobalamin, adenoslycobalamin, hydroxocobalamin and cyanocobalamin.

In a variant of the embodiment there is disclosed a method for detecting microorganisms which may be *Salmonella* spp or *E. coli* spp in a sample. In variants of the embodiment the method comprises the steps of sequentially: culturing the sample in a volume of medium comprising biologically effective amounts of ethanolamine and cobalamin compound; and detecting the *E. coli* spp or *Salmonella* spp in the culture. In the embodiment concentrations of ethanolamine and vitamin B12 are chosen in accordance with other embodiments. In embodiments the culture is incubated for a suitable time under suitable temperature and other conditions to allow the growth of the microorganism of interest prior to detecting the microorganism. In particular embodiments the detecting comprises detecting the bacteria by using PCR, lectins, simple diffusion, lateral diffusion, immunological detection, lateral flow, or flow through methods or may use any other suitable detecting methodology.

After culturing the microorganisms in the media according to an embodiment for a suitable time period under suitable culture conditions, the presence of the microorganism of interest is detected by any one of a range of methods readily apparent to those skilled in the art. Such methods include but are not limited to PCR detection, real time PCR detection, lectin binding, simple diffusion, lateral diffusion, immunological detection, lateral flow, or flow through methods. Without limitation, immunological methods include immunoprecipitation, blotting, immunoradioassay or immuno precipitation associated with magnetic ligands, or may comprise any other suitable immunological methods. In particular embodiments an aliquot of the culture is heated or otherwise treated to kill the microorganism before testing. The heated sample is processed through the desired methodology to identify the presence of antigents or nucleic acid sequences diagnostic of the microorganism of interest.

In one embodiment the medium is used in combination with FoodChek's proprietary testing methodology. Such methodology is herein referred to as MICT. Broadly, in one embodiment of the MICT process, an aliquot of the enriched culture may be heated to kill the target analyte. The heated sample is loaded in a lateral flow cassette, which is composed of a sample/conjugate pad containing nano-sized magnetic particles conjugated to an antibody that will bind the pathogen's antigen. The tests also contain a second antibody in a narrow strip called the capture zone. Capillary flow takes the loaded liquid through the sample pad to the conjugate pad, where the target bacteria bind to the antibody-coated particles. This immune complex flows into the test strip to the capture zone. The result is an accumulation of magnetic particles in the capture zone. If the target pathogen is absent, immune complexes do not form, particles do not accumulate at the capture line, and the test result is negative. Further downstream, a control line that has been stripped in similar fashion but with a different reagent verifies that the test was performed correctly and that the reagents are still active. The cassette is read in an instrument capable of detecting low concentrations of magnetic particles. The detector senses small changes in a magnetic field along the test strip as it passes under a group of sensing coils. The coils are wound in alternating directions so that a characteristic signal profile is generated by the presence of magnetic particles bound to test or control lines. The instrument compares the detection signal with a positive threshold value encoded in the bar code stuck on each individual cassette, and then reports a positive or negative result. The results are displayed on the instrument's liquid crystal display screen and printed, or transferred to a related computer. In addition to all analysis parameters, the bar code also encodes the test name, lot number, and expiration date, which are printed along with the test result. Embodiments of the MICT methods and apparatuses are set forth in one or more of U.S. Pat. No. 7,323,139, U.S. Pat. No. 6,927,570, U.S. Pat. No. 6,607,922, U.S. Pat. No. 6,597,176, U.S. Pat. No. 6,518,747, U.S. Pat. No. 6,483,303, U.S. Pat. No. 6,046,585, U.S. Pat. No. 6,275,031, U.S. Pat. No. 6,437,563, the entire disclosures of which are hereby incorporated herein by reference. Those skilled in the art will readily understand that a wide variety of alternative testing methodologies may be used.

Media according to embodiments can replace at least the first enrichment step in standard protocols for the isolation and identification of Salmonella.

In embodiments it is possible to reach the levels of target microorganism required for some current detection technologies (i.e. about $10^3$ to $10^4$ cfu/ml) in approximately 7 h of incubation from an initial innoculum that may comprise as little as about 1 cfu. In other embodiments it may be possible to reach such levels. In embodiments the detecting may use MICT processes. In embodiments the initial sample may be meat and the sample may be about 375 g of meat however those skilled in the art will recognise that samples of any suitable size and nature may be selected for particular purposes.

EXAMPLES

The following examples are presented as illustrations of the embodiments and do not limit the scope of the subject matter of the various embodiments claimed.

Table 5 shows the formula for a medium for culturing Salmonella bacteria, also referred to as Actero*Salmonella*/STEC Enrichment Media.

The composition and use of a medium according to the embodiment is as follows. Suspend 14.2 g of powdered medium constituents in 1 liter of distilled water. Dispense into a final container and sterilize by autoclaving at 121° C. for 15 minutes. Cool to room temperature. Prior to use, add 2 mL per liter of ethanolamine solution (supplement 1) and 0.5 mL per liter of vitamin B12 (supplement 2). Mix well. The pH of the medium is between 7.9 and 8.5, with a target value of about 8.2.

For Quality Control

Performance: Test 10 mL per liter of medium prepared by inoculating with S. *Typhimurium* ATCC 14028 and E. *coli* O157:H7 ATCC 43895. Both should grow in the medium after a suitable incubation period. The negative control is to incubate the same medium for the same or a longer time period without any inoculant. There should be no bacterial or microorganism growth evident.

When the mixture (also referred to as "base" or "core" medium or broth) has cooled, the ethanolamine and Vitamin B12 are added. Currently the ethanolamine and Vitamin B12 are added to the medium just before use. It will be understood by those skilled in the art that the vitamin solution and ethanolamine should be sterilised before use. In practice the vitamin B12 solution is prepared by mixing 1 mg per ml of water (1 mg/ml) or 1 mg per ml (1 mg/ml) and the ethanolamine and the vitamin B12 solution are filter-sterilized.

Those skilled in the art will also readily understand that for convenience, the base broth or the complete broth may be prepared as a concentrate and diluted with sterile water when desired for use.

Testing Methodology

A sample is prepared for 325 g composited ground beef samples.

1. Pre-warm media base to 39° C. by holding media overnight (10-20 hours) in an incubator or for a few hours in a water bath.
2. Immediately prior to enrichment add 2 mL of ethanolamine and 500 µL of a solution of 1 mg/mL of B12 vitamin to 1 L of pre-warmed media base. Mix thoroughly by swirling and inverting.
3. Add two parts of pre-warmed media (containing both ethanolamine and B12 vitamin) to one part of sample (Ex. 650 mL of supplemented medium to 325 g of ground beef) in a filter-equipped stomacher bag.
4. Stomach sample for 30 seconds at 150 rpm in a Stomacher® 3500.
5. Close bag loosely and incubate the samples for enrichments for 7 hours at 39° C. in a water bath. If a large

TABLE 5

Composition of a Core Medium according to the example

| Product | Manufacturer (Cat. #) | Qty (g/L) |
|---|---|---|
| Deionised Water | | 1 L |
| Calcium Chloride Dihydrate ($CaCl_2 \cdot 2H_2O$) | BDH Chemicals (M061932) | 0.013 |
| Potassium Phosphate Monobasic ($KH_2PO_4$) | Sigma (P5655) | 3 |
| Magnesium Sulphate Anhydrous ($MgSO_4$) | BDH Chemicals (BDH0246) | 0.12 |
| Sodium Chloride (NaCl) | Fisher Scientific (S671) | 0.5 |
| Bacto TM Yeast Extract | BD Biosciences (212750) | 3 |
| Sodium Phosphate Dibasic ($Na_2HPO_4$) | American Chemicals LTD (7558-79-4) | 6 |
| Sodium Pyruvate (CH3COCOONa) | Sigma (Fluka) 15990 | 1 g |
| Ferrous sulphate ($FeSO_4$) | Sigma-Aldrich | 0.019 g |
| Citric acid ($C_6H_8O_7$) | Sigma/Aldrich (251275) | 0.547 g |
| (Total of above ingredients) | | (14.2 g) |
| Cool the core medium and add the following: | | |
| | | Qty mL |
| Ethanolamine (solution) 16.6M (supplement 1) | Sigma (E0135) | 2 |
| Vitamin B12 solution 1 mg/ml (Supplement 2) | Sigma (V6629) | 0.5 | number of samples are to be analyzed, verify that the temperature of the water between the sample bags reaches 39° C. before starting to record the incubation time. It is important to precisely control the enrichment period to obtain valuable and accurate results.

6. After 7 hours remove the samples from the water bath and re-suspend the contents.

Once the sample has been prepared, *Salmonella* spp. or *E. coli* spp may be detected using FoodChek's analytical process as described above, or using any conventional testing methods. In one example the *Salmonella* spp. may be detected using suitable selective antibodies. In embodiments using suitably sensitive detection methods, sensitivity may be 1 cfu/325 g of ground beef. Such suitably sensitive detection methods may comprise the use of selective antibodies.

Further Examples

Supplies and Reagents:

Distilled/deionized, sterile water. Any source; Tetrathionate Broth (TT)—Quelab Laboratories, Quebec, Canada; Rappaport-Vassiliadis Soya Peptone Broth (RVS)—Oxoid, Hampshire, England; Rappaport-Vassiliadis Broth (RV); Xylose Lysine Tergitol-4 Agar (XLT4)—Difco Becton Dickinson, New Jersey, USA; BG Sulfa Agar (BGS)—Difco Becton Dickinson, New Jersey, USA; Xylose Lysine Deoxycholate agar (XLD)—Quelab Laboratories, Quebec, Canada; Hektoen Enteric agar (HE)—Quelab Laboratories, Quebec, Canada; Triple Sugar Iron (TSI)—Difco Becton Dickinson, New Jersey, USA; Lysine Iron Agar (LIA)—BBL Becton Dickinson, New Jersey, USA; *Salmonella* antisera—Difco Becton Dickinson, New Jersey, USA; API 20 E kits for identification of enterobacteriacae—Biomérieux, Marcy-L'etoile, France; Plastic inoculating needles and 10 µL calibrated loops. Any source; Sterile pipets, 10 mL—Any source Apparatus:

Stationary incubator Symphony™ (VWR, USA) or equivalent—Capable of providing 39° C.±0.5; Stationary incubator, model 1555 (VWR, USA) or equivalent.—Capable of providing 35° C.±2.0; Water bath (Polyscience, USA) or equivalent.—Capable of providing 39° C.±0.5; Water bath, circulating, thermostatically controlled (Lindberg/Blue, USA), or equivalent—Capable of providing 42° C.±0.2; Water bath, circulating, thermostatically controlled (Lindberg/Blue, USA), or equivalent—Capable of providing 43° C.±0.2; Micropipette—Capable of accurately dispensing 500 µL—Any source; Top loading balance to weigh 25, 100 and 325 g samples—Any source; Stomacher—Seward model 3500 (Seward, London, England) or equivalent—for thorough mixing of food samples in enrichment broth; Stomacher—Seward Model 400 (Seward, London, England) or equivalent—for thorough mixing of food samples in enrichment broth; Vortex mixer (VWR, USA).

General Preparation of medium: To prepare Actero *Salmonella*/STEC, suspend 14.2 g of the powdered medium in one liter of distilled water and mix well. Dispense into final container and sterilize by autoclaving at 121° C. for 15 min. Cool to room temperature. In some cases it has been found that it is not necessary to autoclave the medium if it is used immediately after preparation but in this case it is preferable to use sterile water to make the medium. Prior to use, add 2 mL of supplement 1 (16.6M ethanolamine) and 0.5 mL of supplement 2 (1 mg/ml vitamin B12) to one liter of the medium core in aseptic condition.

Prepare other media according to the manufacturer's instructions.

Additional materials and reagents: Trypticase Soy agar plates with 5% of sheep blood (blood agar)—BBL Becton Dickinson, New Jersey, USA; TT broth (TT Hajna)—Quelab Laboratories, Quebec, Canada; Tryptone Soya Agar (TSA)—Quelab Laboratories, Quebec, Canada; Tryptone Soya Broth (TSB)—Oxoid, Hampshire, England; Plate Count Agar (PCA); Phosphate Buffered Saline (PBS)—Oxoid, Hampshire, England; Modified Rainbow Agar (mRBA)—Biolog, California, USA; Bismuth Sulfite Agar (BS)—Difco Becton Dickinson, New Jersey, USA; Lactose Broth—Quelab Laboratories, Quebec, Canada; Buffered Peptone Water (BPW)—Fluka Analytical, St-Louis, USA; Isotemp water bath (Fisher Scientific, USA) or equivalent.—Capable of providing 55° C.±0.2. Materials, methods and reagents necessary to perform the reference methods are further detailed in: Chapter 4 entitled Isolation and identification of *Salmonella* from, meat, poultry and eggs products in USDA/FSIS Microbiology Laboratory guidebook, 3rd Edition, Rev. #4, website: fsis.usda.gov/PDF/MLG_4_05.pdf; Chapter 5B entitled Detection and Isolation of non-O157 Shiga-toxin Producing *Escherichia coli* (STEC) from Meat Products in USDA/FSIS Microbiology Laboratory guidebook, 3rd Edition, Rev. #1, website: fsis.usda.gov/PDF/Mlg_5B_01.pdf; Chapter 5 entitled *Salmonella* in FDA Bacterial Analytical Manual, 8th Edition, November 2011 Version, website: fda.gov/Food/ScienceResearch/LaboratoryMethods/BacteriologicalAnalyticalManualBAM/ucm070149.htm Sample Preparation: The sample preparation depends on the type and size of the sample. Thus, the protocol to prepare the sample is chosen to reflect those conditions. Preparation methods for selected sample types are further explained below.

Analysis: The analysis of the samples depends on the types of the samples. Thus, the protocol to prepare the sample should be chosen to reflect the sample type.

Interpretation and Test Result Report: The results are confirmed according the US FDA Bacteriological Analytical Manual Chapter 5 and USDA FSIS Microbiology Laboratory Guidebook Chapters 4.05 and 5B.01. Both of these will be well understood by those skilled in the art and are hereby incorporated herein by reference in their entirety where permissible by law.

Internal Validation Studies:

The following validation studies were conducted:

1. Robustness Studies:

The robustness studies were carried out to evaluate the effect of modifying two parameters: the temperature and the incubation time. The robustness variables and their respective ranges are shown in Table 6.

Methodology:

Each test range condition was evaluated by analysis of the growth of three pure cultures on selective agar plates. *S. typhimurium* ATCC 14028 was chosen as the representative of *Salmonella* spp. and the results were analyzed on XLT4 and BGS agar plates. *E. coli* O157:H7 ATCC 43895 was chosen as a STEC and was analyzed on modified rainbow agar and *E. faecalis* ATCC 19433 was chosen as the non-target strain and was analyzed on XLT4, BGS and modified rainbow agar.

For the three parameters, the strains were streaked on Trypticase Soy Agar with 5% Sheep's Blood (also referred to as Blood Agar) and incubated overnight at 35° C.±1° C. A few colonies of the target strains were transferred to 9 mL of TSB for 6-7 hours at 35° C.±1° C. Each culture was diluted 1:10 in fresh TSB and was incubated overnight at the same temperature. These cultures were then diluted to obtain a fractional inoculation level (0.5 CFU per sample) in the Actero *Salmonella*/STEC Actero *Salmonella*/STEC broth. The cultures were grown using the standard protocol except for the parameter evaluated.

For the non-target strain the same methodology was used for culturing except that the level of inoculation was 10 times higher. Ten replicates of each target and 5 replicates of the non-target were tested for each parameter.

Results:

According to the POD (probability of detection) analysis performed on the results, there were no significant differences observed (Table 6). The confidence interval between the dPOD (difference in probability of detection) of extreme conditions contains a zero, so there is not a statistical difference between each parameter. So the minor changes of temperature and times tested did not affect significantly the ability of the Actero *Salmonella*/STEC to recover *S. typhimurium* ATCC 14028 and *E. coli* O157:H7 ATCC 43895. Presence of non-target strain *E. faecalis* ATCC 19433 in the Actero *Salmonella*/STEC samples was not detected in any case (data not shown).

2. Inclusivity Studies:

One hundred and nine (109) *Salmonella* strains (Table 7), representing almost all species of *Salmonella* (including lactose positive strains) and 50 Shiga toxin-producing *E. coli* strains (STEC) (Table 8), representing STEC species (strains belonging to the "big six" and to *E. coli* O157 family) were analyzed to test the capacity of the broth to enrich *Salmonella* spp. and STEC strains.

Methodology:

All *Salmonella* spp. and STEC strains were streaked on Blood Agar and incubated overnight at 35° C. A few colonies were transferred to 10 mL of TSB for 6-7 hours at 35° C. Each culture was diluted 1:10 in fresh TSB and incubated overnight at the same temperature. The culture was then diluted to inoculate a low concentration (between 1.0 and 20 CFU/mL) of the strain in the Actero *Salmonella*/STEC broth. Each strain was cultured in triplicate. The cultures were grown at 39±0.5° C. for 7 h in a water bath. The growth of *Salmonella* strains was analyzed by streaking 10 µL of each sample on *Salmonella* selective agar plates (XLT4, BGS, XLD and HE). For STEC strains, the growth was confirmed by streaking on modified Rainbow Agar plates.

Results:

Results from the Inclusivity Study are summarized in Tables 7 and 8 respectively for *Salmonella* spp. and STEC strains. Among the 110 strains of *Salmonella* tested in the Actero *Salmonella*/STEC broth, 6 shows a slow growth and 3 didn't grow. In total, 106 of 109 (97.2%) *Salmonella* strains grow in the Actero *Salmonella*/STEC broth and could be identified on specific selective agar plates. Concerning the STEC species, the 50 (100%) strains tested grow in the Actero *Salmonella*/STEC broth and could be identified on selective agar plate, but 2 shows a slower growth compared to the others. So, overall, 98.1% of the target strains were identified in the conditions used for the enrichment.

TABLE 6

Actero *Salmonella*/STEC Method Robustness Results

| Parameter | Condition A | Condition B | Strain | $N^a$ | $X^b$ | $POD_A{}^c$ | 95% CI | X | $POD_B{}^d$ | 95% CI | $dPOD_{AB}{}^e$ | 95% CI$^f$ |
|---|---|---|---|---|---|---|---|---|---|---|---|---|
| 39° C. water bath | 6 h | 7.5 h | *S. Typhimurium* | 10 | 4 | 0.4 | (0.168, 0.687) | 2 | 0.2 | (0.057, 0.51) | 0.2 | (−0.092, 0.521) |
|  |  |  | *E. coli* O157:H7 | 10 | 5 | 0.5 | (0.237, 0.763) | 4 | 0.4 | (0.168, 0.687) | 0.1 | (−0.285, 0.451) |
| 39° C. incubator | 16 h | 20 h | *S. Typhimurium* | 10 | 3 | 0.3 | (0.108, 0.603) | 4 | 0.4 | (0.168, 0.687) | −0.1 | (−0.446, 0.282) |
|  |  |  | *E. coli* O157:H7 | 10 | 5 | 0.5 | (0.237, 0.763) | 3 | 0.3 | (0.108, 0.603) | 0.2 | (−0.202, 0.526) |
| 7 h water bath | 38° C. | 40° C. | *S. Typhimurium* | 10 | 5 | 0.5 | (0.237, 0.763) | 6 | 0.6 | (0.312, 0.831) | −0.1 | (−0.391, 0.290) |
|  |  |  | *E. coli* O157:H7 | 10 | 4 | 0.4 | (0.168, 0.687) | 2 | 0.2 | (0.057, 0.510) | 0.2 | (−0.134, 0.521) |
| 18 h incubator | 38° C. | 40° C. | *S. Typhimurium* | 10 | 2 | 0.2 | (0.057, 0.510) | 6 | 0.6 | (0.313, 0.832) | −0.4 | (−0.672, 0.023) |
|  |  |  | *E. coli* O157:H7 | 10 | 5 | 0.5 | (0.237, 0.763) | 5 | 0.5 | (0.237, 0.763) | 0 | (−0.372, 0.372) |

$^a$N = Number of test potions
$^b$x = Number of positive test portions
$^c$POD$_A$ = Condition A positive outcomes divided by the total number of trials
$^d$POD$_B$ = Condition B positive outcomes divided by the total number of trials
$^e$dPOD$_{AB}$ = Difference between condition A and condition B POD values
$^f$95% CI = If the confidence interval of a dPOD does not contain zero, then the difference is statistically significant at the 5% level

TABLE 7

_Salmonella spp. list - Inclusivity study results_

| # | Strain number | Genus | Subspecies | Serotype | Sero-group | Origin | Source[a] | Result |
|---|---|---|---|---|---|---|---|---|
| 1 | MSR0042 | Salmonella | enterica | Paratyphi A | A | N/A | LFZ (PHAC) | +* |
| 2 | MSR0001 | Salmonella | enterica | Kiambu | B | Chicken breast | CIPARS (PHAC) | + |
| 3 | MSR0002 | Salmonella | enterica | Schwarzengrund | B | Chicken thighs | CIPARS (PHAC) | + |
| 4 | MSR0003 | Salmonella | enterica | Heidelberg | B | Chicken thighs | CIPARS (PHAC) | + |
| 5 | 12-047 | Salmonella | enterica | Heidelberg | B | Raw ground chicken | Maxivet inc. | + |
| 6 | MSR0010 | Salmonella | enterica | Typhimurium var. Copenhagen | B | Chicken wings | CIPARS (PHAC) | + |
| 7 | MSR0013 | Salmonella | enterica | Agona | B | Chicken thighs | CIPARS (PHAC) | + |
| 8 | MSR0017 | Salmonella | enterica | Indiana | B | Chicken wings | CIPARS (PHAC) | + |
| 9 | MSR0026 | Salmonella | enterica | Saintpaul | B | Water-Fish | MAPAQ | + |
| 10 | MSR0031 | Salmonella | enterica | Stanley | B | LLZ CQ 2008 | MAPAQ | + |
| 11 | MSR0032 | Salmonella | enterica | Bredeney | B | Turkey liver | MAPAQ | + |
| 12 | MSR0034 | Salmonella | enterica | Paratyphi B var. Java | B | Water-Turtle | MAPAQ | + |
| 13 | MSR0044 | Salmonella | enterica | Chester | B | Porcine | LFZ (PHAC) | + |
| 14 | MSR0065 | Salmonella | enterica | Haifa | B | N/A | SGSC | + |
| 15 | MSR0084 | Salmonella | enterica | Brandenburg | B | Swine feaces | Maxivet inc. | + |
| 16 | MSR0088 | Salmonella | enterica | Derby | B | Swine feaces | Maxivet inc. | + |
| 17 | MSR0079 | Salmonella | enterica | California 4:gmt:— | B | Swine feaces | Maxivet inc. | + |
| 18 | MSR0111 | Salmonella | enterica | Typhimurium | B | ATCC 14028 | ND | + |
| 19 | MSR0023 | Salmonella | enterica | I4,[5],12i:— | B | Swine jejunum | MAPAQ | + |
| 20 | MSR0008 | Salmonella | enterica | Braenderup | C1 | Chicken thighs | CIPARS (PHAC) | + |
| 21 | MSR0012 | Salmonella | enterica | Ohio | C1 | Chicken thighs | CIPARS (PHAC) | + |
| 22 | MSR0014 | Salmonella | enterica | Thompson | C1 | Chicken thighs | CIPARS (PHAC) | +* |
| 23 | MSR0015 | Salmonella | enterica | Mbandaka | C1 | Chicken thighs | CIPARS (PHAC) | + |
| 24 | MSR0114 | Salmonella | enterica | I:6,7,14:z10:— | C1 | Fish flour | Maxivet inc. | + |
| 25 | MSR0082 | Salmonella | enterica | I:6,7:—:1,5 | C1 | Environmental-Poultry | Maxivet inc. | + |
| 26 | MSR0018 | Salmonella | enterica | Montevideo | C1 | Chicken thighs | CIPARS (PHAC) | + |
| 27 | MSR0019 | Salmonella | enterica | Infantis | C1 | Chicken thighs | CIPARS (PHAC) | + |
| 28 | MSR0030 | Salmonella | enterica | Oranienburg | C1 | Environmental-Poultry | MAPAQ | + |
| 29 | MSR0048 | Salmonella | enterica | Virchow | C1 | Shrimp | LFZ (PHAC) | + |
| 30 | MSR0057 | Salmonella | enterica | Lille | C1 | N/A | MAPAQ | + |
| 31 | MSR0076 | Salmonella | enterica | Tenessee | C1 | Fish flour | Maxivet inc. | + |
| 32 | MSR0110 | Salmonella | enterica | Rissen | C1 | Flour | Maxivet inc. | + |
| 33 | MSR0205 | Salmonella | enterica | Paratyphi C | C1 | N/A | SGSC | +* |
| 34 | MSR0168 | Salmonella | indica | VI:6,7:z41:1,7 | C1 | N/A | SGSC | + |
| 35 | MSR0009 | Salmonella | enterica | Hadar | C2 | Chicken thighs | CIPARS (PHAC) | + |
| 36 | MSR0016 | Salmonella | enterica | Litchfield | C2 | Chicken wings | CIPARS (PHAC) | + |
| 37 | MSR0021 | Salmonella | enterica | Newport | C2 | Cat | MAPAQ | + |
| 38 | MSR0025 | Salmonella | enterica | Muenchen | C2 | Swine | MAPAQ | + |
| 39 | MSR0104 | Salmonella | enterica | Molade | C2 | Swine feces | Maxivet inc. | + |
| 40 | MSR0045 | Salmonella | enterica | Blockley | C2 | Chicken | LFZ (PHAC) | + |
| 41 | MSR0047 | Salmonella | enterica | Bovismordificans | C2 | Porcine | LFZ (PHAC) | + |
| 42 | MSR0006 | Salmonella | enterica | Albany | C3 | Chicken thighs | CIPARS (PHAC) | + |
| 43 | MSR0007 | Salmonella | enterica | Kentucky | C3 | Chicken thighs | CIPARS (PHAC) | + |
| 44 | MSR0063 | Salmonella | enterica | Emek | C3 | N/A | SGSC | + |
| 45 | MSR0004 | Salmonella | enterica | Enteritidis | D1 | Chicken wings | CIPARS (PHAC) | + |
| 46 | MSR0022 | Salmonella | enterica | Javiana | D1 | LLZ CQ 2010 | MAPAQ | + |
| 47 | MSR0028 | Salmonella | enterica | Dublin | D1 | LLZ | MAPAQ | + |
| 48 | MSR0064 | Salmonella | enterica | Gallinarum | D1 | Human | SGSC | − |
| 49 | MSR0204 | Salmonella | enterica | Typhi | D1 | N/A | SGSC | − |
| 50 | MSR0011 | Salmonella | enterica | Anatum | E1 | Chicken thighs | CIPARS (PHAC) | + |
| 51 | MSR0029 | Salmonella | enterica | Muenster | E1 | Bovine feaces | MAPAQ | + |
| 52 | MSR0046 | Salmonella | enterica | Meleagridis | E1 | N/A | ASPC | + |
| 53 | MSR0091 | Salmonella | enterica | Give | E1 | Fish flour | Maxivet inc. | + |
| 54 | MSR0099 | Salmonella | enterica | Orion | E1 | Meat flour | Maxivet inc. | + |
| 55 | MSR0103 | Salmonella | enterica | Lexington | E1 | Swine feces | Maxivet inc. | + |

TABLE 7-continued

Salmonella spp. list - Inclusivity study results

| # | Strain number | Genus | Subspecies | Serotype | Sero-group | Origin | Source[a] | Result |
|---|---|---|---|---|---|---|---|---|
| 56 | MSR0020 | Salmonella | enterica | Liverpool | E4 | Chicken breast | CIPARS (PHAC) | +* |
| 57 | MSR0089 | Salmonella | enterica | Krefeld | E4 | N/A | N/A | + |
| 58 | MSR0106 | Salmonella | enterica | Dessau | E4 | Fish flour | Maxivet inc. | + |
| 59 | MSR0112 | Salmonella | enterica | Senftenberg | E4 | ATCC 8400 | ND | + |
| 60 | MSR0038 | Salmonella | enterica | Rubislaw | F | Water-Terrarium | MAPAQ | + |
| 61 | MRS0173 | Salmonella | diarizonae | IIIb:11:k:z53 | F | Unknown | LFZ (PHAC) | + |
| 62 | MSR0170 | Salmonella | indica | VI:11:a:1,5 | F | N/A | SGSC | + |
| 63 | MSR0037 | Salmonella | enterica | Poona | G1 | Chameleon feaces | MAPAQ | + |
| 64 | MSR0005 | Salmonella | enterica | Worthington | G2 | Chicken thighs | CIPARS (PHAC) | + |
| 65 | MSR0043 | Salmonella | enterica | Mishmarhaemek | G2 | Porcine | LFZ (PHAC) | + |
| 66 | MSR0074 | Salmonella | enterica | Cubana | G2 | Flour | Maxivet inc. | + |
| 67 | MSR0102 | Salmonella | enterica | Havana | G2 | Fish flour | Maxivet inc. | + |
| 68 | MSR0050 | Salmonella | enterica | Beaudesert | H | Bearded dragon | LFZ (PHAC) | + |
| 69 | MSR0186 | Salmonella | indica | VI:1,6,14,25:a:e,n,x | H | Coconut | SGSC | + |
| 70 | MSR0067 | Salmonella | enterica | Saphra | I | N/A | LFZ (PHAC) | + |
| 71 | MSR0049 | Salmonella | enterica | Carmel | J | N/A | LFZ (PHAC) | + |
| 72 | MSR0071 | Salmonella | enterica | Cerro | K | Fish flour | Maxivet inc. | + |
| 73 | MSR0078 | Salmonella | enterica | Ruiru 21:y:x | L | Fish flour | Maxivet inc. | + |
| 74 | MSR0040 | Salmonella | enterica | Pomona | M | Water-Fish | MAPAQ | + |
| 75 | MSR0092 | Salmonella | enterica | Urbana | N | N/A | N/A | + |
| 76 | MSR0041 | Salmonella | enterica | Ealing | O | Soy | Maxivet inc. | + |
| 77 | MSR0066 | Salmonella | enterica | Monschaui | O | N/A | LFZ (PHAC) | + |
| 78 | MSR0068 | Salmonella | enterica | Lansing | P | N/A | LFZ (PHAC) | + |
| 79 | MSR0185 | Salmonella | diarizonae | IIIb:38:(k):z35:— | P | Human | SGSC | + |
| 80 | MSR0039 | Salmonella | enterica | Wandsworth | Q | Aquatic moss | MAPAQ | + |
| 81 | MSR0060 | Salmonella | enterica | Tilene | R | N/A | SGSC | + |
| 82 | MSR0077 | Salmonella | enterica | Johannesburg | R | Flour | Maxivet inc. | + |
| 83 | MSR0167 | Salmonella | | V:1,40:z35:— | R | Food | SGSC | +* |
| 84 | MSR0187 | Salmonella | indica | VI:41:b:1,7 | S | Opossum | SGSC | + |
| 85 | MSR0055 | Salmonella | enterica | Waycross | S | N/A | LFZ (PHAC) | + |
| 86 | MSR0056 | Salmonella | enterica | Kingabwa | U | Lizard | LFZ (PHAC) | + |
| 87 | MSR0069 | Salmonella | enterica | Niarembe | V | N/A | LFZ (PHAC) | + |
| 88 | MSR0166 | Salmonella | | V:44:z39:— | V | Food | SGSC | + |
| 89 | MSR0054 | Salmonella | houtenae | IV:45:g,z51:— | W | Chicoree leak | LFZ (PHAC) | + |
| 90 | MSR0053 | Salmonella | enterica | Bootle | X | Shrimp | LFZ (PHAC) | + |
| 91 | MSR0052 | Salmonella | arizonae | IIIa:48:z4,z24:— | Y | Feline | LFZ (PHAC) | + |
| 92 | MSR0181 | Salmonella | arizonae | IIIa:48:z4,z24:— | Y | Human | SGSC | + |
| 93 | MSR0182 | Salmonella | diarizonae | IIIb:48:i:z | Y | Human | SGSC | + |
| 94 | MSR0051 | Salmonella | houtenae | IV:50:z4,z23:— | Z | N/A | LFZ (PHAC) | + |
| 95 | MSR0062 | Salmonella | houtenae | IV:50:g,z51 (Wassenaar) | Z | N/A | LFZ (PHAC) | + |
| 96 | MSR0184 | Salmonella | diarizonae | IIIb:50:k:z | Z | Human | SGSC | + |
| 97 | MSR0059 | Salmonella | arizonae | IIIa:51:z4,z23:— | 51 | N/A | SGSC | + |
| 98 | MSR0163 | Salmonella | salamae | II:58:d:z6 | 58 | Human | SGSC | + |
| 99 | MSR0171 | Salmonella | salamae | II:57:z29:— | 57 | Unknown | LFZ (PHAC) | − |
| 100 | MRS0174 | Salmonella | diarizonae | IIIb:60:z52:z53 | 60 | Unknown | LFZ (PHAC) | + |
| 101 | MSR0061 | Salmonella | salamae | II:60:g,m,t:z6 (Setubal) | 60 | N/A | SGSC | + |
| 102 | MSR0183 | Salmonella | diarizonae | IIIb:61:k:1,5,(7) | 61 | Human | SGSC | +* |
| 103 | MSR0164 | Salmonella | arizonae | IIIa:62:z36:— | 62 | Human | SGSC | + |
| 104 | MSR0058 | Salmonella | | V 66:$z_{35}$:—(Maregrosso) | 66 | N/A | SGSC | + |
| 105 | MSR0165 | Salmonella | diarizonae | IIIb:65:(k):z | 65 | Human | SGSC | + |
| 106 | MSR0100 | Salmonella | enterica | I:40:b:— | — | Flour | Maxivet inc. | + |
| 107 | MSR0101 | Salmonella | enterica | I:rough-O:r:1,2 | — | Environmental-Poultry | Maxivet inc. | + |
| 108 | MSR0113 | Salmonella | enterica | I:6,7:—:e,n,z15 | — | Poultry | Maxivet inc. | + |
| 109 | 12-055 | Salmonella | enterica | I:Rough-o:y:e,n,x | — | Fish flour | Maxivet inc. | + |

[a]LFZ (PHAC): Laboratory for Foodborne Zoonose (Public Health Agency of Canada), Guelph, Canada, SGSC: *Salmonella* Genetic Stock Center, Department of Biological Sciences, University of Calgary, Canada, MAPAQ: Ministry of Agriculture, Fisheries and Food of Quebec, Quebec (QC), Canada. CIPARS (PHAC): Canadian Integrated Program for Antimicrobial Resistance Surveillance, (Public Health Agency of Canada), Saint-Hyacinthe, Canada. Maxivet inc: Saint-Hyacinthe, Quebec, Canada + Presence of typical colonies of *Salmonella* spp. on *Salmonella* selective agar plates +* Presence of typical colonies of *Salmonella* spp. on *Salmonella* selective agar plates but the observed growth was slower.

− No growth was observed on either of selective agar plate for the particular *Salmonella* strain.

TABLE 8

STEC list - Inclusivity study results

| # | Strain number | Genus and species | Strain | Source[a] | Result |
|---|---|---|---|---|---|
| 1 | MSR0144 | *Escherichia coli* O26 | Ovine (13918) | EcL | + |
| 2 | MSR0136 | *Escherichia coli* O26:K60 | field isolate | EcL | + |
| 3 | MSR0207 | *Escherichia coli* O26:H11 | Bovine (EC19960464) | PHAC | + |
| 4 | MSR0208 | *Escherichia coli* O26:H11 | Human (EC19970119) | PHAC | + |
| 5 | MSR0209 | *Escherichia coli* O45:H2 | Bovine (EC19940040) | PHAC | + |
| 6 | MSR0210 | *Escherichia coli* O45:H2 | Human (EC19970074) | PHAC | + |
| 7 | MSR0211 | *Escherichia coli* O45:H2 | Human (EC19970086) | PHAC | + |
| 8 | MSR0212 | *Escherichia coli* O45:H2 | Human (EC19970358) | PHAC | + |
| 9 | MSR0138 | *Escherichia coli* O103 | Ovine (13857) | EcL | + |
| 10 | MSR0139 | *Escherichia coli* O103 | Ovine (13858) | EcL | + |
| 11 | MSR0140 | *Escherichia coli* O103 | Ovine (13862) | EcL | + |
| 12 | MSR0141 | *Escherichia coli* O103 | Ovine (13863) | EcL | + |
| 13 | MSR0142 | *Escherichia coli* O103 | Ovine (13864) | EcL | + |
| 14 | MSR0143 | *Escherichia coli* O103 | Ovine (13897) | EcL | + |
| 15 | MSR0145 | *Escherichia coli* O103 | Ovine (13926) | EcL | + |
| 16 | MSR0146 | *Escherichia coli* O103 | Ovine (13928) | EcL | + |
| 17 | MSR0137 | *Escherichia coli* O103 | Bovine (10368) | EcL | + |
| 18 | MSR0135 | *Escherichia coli* O103:H2 | field isolate | *E. coli* ref. center | + |
| 19 | MSR0134 | *Escherichia coli* O111:H8 | field isolate | *E. coli* ref. center | + |
| 20 | MSR0213 | *Escherichia coli* O111:H8 | Bovine (EC19930467) | PHAC | + |
| 21 | MSR0214 | *Escherichia coli* O111:H8 | Bovine (EC20000612) | PHAC | + |
| 22 | MSR0215 | *Escherichia coli* O111:NM | Human (EC20000927) | PHAC | +* |
| 23 | MSR0216 | *Escherichia coli* O121:H19 | Human (EC19960807) | PHAC | + |
| 24 | MSR0217 | *Escherichia coli* O121:H19 | Human (EC19990161) | PHAC | + |
| 25 | MSR0218 | *Escherichia coli* O121:H19 | Human (EC20020234) | PHAC | + |
| 26 | MSR0219 | *Escherichia coli* O121:H19 | Bovine (EC20040083) | PHAC | + |
| 27 | MSR0220 | *Escherichia coli* O145:NM | Human (EC20020231) | PHAC | + |
| 28 | MSR0221 | *Escherichia coli* O145:NM | Human (EC19970355) | PHAC | + |
| 29 | MSR0222 | *Escherichia coli* O145:H25 | Human (EC19990166) | PHAC | + |
| 30 | MSR0223 | *Escherichia coli* O145:NM | Human (EC19990324) | PHAC | + |
| 31 | MSR0293 | *Escherichia coli* O157:H7 | ATCC 35150 | EcL | + |
| 32 | MSR0294 | *Escherichia coli* O157:H7 | ATCC 43895 (isolated from ground beef) | EcL | + |
| 33 | MSR0295 | *Escherichia coli* O157:H7 | Isolated from ground beef (H3-FC-2) | Unknown | + |
| 34 | MSR0296 | *Escherichia coli* O157:H7 | field isolate (CRDA 506) | CRDA | +* |
| 35 | MSR0297 | *Escherichia coli* O157:H7 | Isolated from sausage (California USA)(CRDA 507) | CRDA | + |
| 36 | MSR0133 | *Escherichia coli* O157:H7 | Isolated from salami (CRDA 508) | CRDA | + |
| 37 | MSR0298 | *Escherichia coli* O157:H7 | From an alimentary toxi-infection (USA, 1993) (CRDA 509) | CRDA | + |
| 38 | MSR0299 | *Escherichia coli* O157:H7 | From an alimentary toxi-infection (MEC-1) | LSPQ | + |
| 39 | MSR0300 | *Escherichia coli* O157:H7 | From an alimentary toxi-infection(MEC-2) | LSPQ | + |
| 40 | MSR0301 | *Escherichia coli* O157:H7 | From an alimentary toxi-infection (MEC-3) | LSPQ | + |
| 41 | MSR0302 | *Escherichia coli* O157:H7 | From an alimentary toxi-infection (MEC-4) | LSPQ | + |
| 42 | MSR0303 | *Escherichia coli* O157:H7 | From an alimentary toxi-infection(MEC-5) | LSPQ | + |
| 43 | MSR0304 | *Escherichia coli* O157:H7 | From an alimentary toxi-infection(MEC-6) | LSPQ | + |
| 44 | MSR0305 | *Escherichia coli* O157:H7 | 93111 (MEC27) | PHAC | + |
| 45 | MSR0306 | *Escherichia coli* O157:H7 | OK1 (MEC28) | PHAC | + |
| 46 | MSR0307 | *Escherichia coli* O157:H7 | 278F1 (MEC21) | PHAC | + |
| 47 | MSR0308 | *Escherichia coli* O157:H7 | 279F1 (MEC29) | PHAC | + |
| 48 | MSR0309 | *Escherichia coli* O157:H7 | 237F1 (MEC18) | PHAC | + |
| 49 | MSR0310 | *Escherichia coli* O157:H7 | 235F1 (MEC19) | PHAC | + |
| 50 | MSR0311 | *Escherichia coli* O157:H7 | D103F5 (MEC23) | PHAC | + |

*These bacteria grow slower compared to the others
[a]PHAC: Public Health Agency of Canada, Guelph, Canada. EcL: *E. coli* Laboratory, Faculty of Veterinary Medicine, Saint-Hyacinthe, Québec (QC), Canada. *E. coli* ref. center: *E. coli* Reference Center, The Pennsylvania State University, Pennsylvania, USA. LSPQ: Laboratoire de Santé publique du Québec, Saint-Anne-de-Bellevue, Québec (QC), Canada. CRDA: Centre de Recherche et Développement sur les Aliments, Saint-Hyacinthe, Québec (QC), Canada
+ Presence of typical colonies of STEC on rainbow agar.
+* Presence of typical colonies of STEC on modified rainbow agar but the observed growth was slower.
− No growth on either form of selective agar plates for the specific strain of *salmonella*.

3. Exclusivity Studies:

Thirty one (31) non-target strains, chosen as close genetic relatives of *Salmonella* and *E. coli* and species that are found in the same environment, were tested in the Actero *Salmonella*/STEC Enrichment Media. They represent 25 different genera of bacteria and yeasts.

Methodology:

Each non-target strain was streaked on Blood Agar and incubated overnight at 35° C. Then, each non-target strain was cultured in their optimal condition. Each bacterial suspension was diluted to inoculate the Actero *Salmonella*/STEC broth with an average concentration 10 times higher than what was used for the target strains. This step was done in triplicate. Their growth in the Actero *Salmonella*/STEC broth was tested at 39±0.5° C. for 7 h in a water bath and 18 h in an incubator. They were then analyzed on specific selective agar plates for *Salmonella* and STEC to verify if they were growing and if the Actero *Salmonella*/STEC broth, for any reason, causes a change in the phenotype that could lead to a misinterpretation of the results.

Results:

Exclusivity results are summarized in Table 9. Most non-target strains did not grow on the selective agar plates. From those where growth could be observed, none of them showed a phenotype that can resemble *Salmonella* or STEC strains, or could lead to a misinterpretation of the results on selective agar plates.

TABLE 9

Non-*Salmonella*/non-STEC bacteria included in exclusivity testing

| No. | Genus | Species | Strain | Source[a] | Result |
|---|---|---|---|---|---|
| 1 | Alcaligenes | faecalis | ATCC 8750 | FMV | Atypical growth |
| 2 | Acinetobacter | baumannii | ATCC 19606 | SGSC | No growth |
| 3 | Streptococcus | agalactiae | ATCC 13812 | FMV | No growth |
| 4 | Bacillus | subtilis | field isolate | Maxivet inc. | No growth |
| 5 | Bacillus | cereus | ATCC 14579 | FMV | No growth |
| 6 | Candida | albicans | ATCC 24433 | FMV | No growth |
| 7 | Carnobacterium | divergens | ATCC 35677 | ARS | No growth |
| 8 | Citrobacter | freundii | ATCC 8090 | FMV | Atypical growth |
| 9 | Citrobacter | amalonaticus | Field isolate | SGSC | Atypical growth |
| 10 | Enterobacter | cloacae | ATCC 23355 | FMV | Atypical growth |
| 11 | Enterococcus | faecalis | ATCC 19433 | FMV | Atypical growth |
| 12 | Enterococcus | faecium | ATCC 8459 | ARS | No growth |
| 13 | Hafnia | alvei | ATCC 13337 | FMV | No growth |
| 14 | Klebsiella | pneumoniae | ATCC 13883 | FMV | Atypical growth |
| 15 | Kluyvera | spp. | Field isolate | SGSC | Atypical growth |
| 16 | Kocuria | rhizophila | ATCC 9341 | FMV | No growth |
| 17 | Lactobacillus | acidophilus | ATCC 314 | FMV | No growth |
| 18 | Listeria | monocytogenes | ATCC 43236 | FMV | No growth |
| 19 | Morganella | morganii | ATCC 25830 | FMV | Atypical growth |
| 20 | Proteus | mirabilis | ATCC 29906 | FMV | Atypical growth |
| 21 | Pseudomonas | fluorescens | field isolate | FMV | No growth |
| 22 | Pseudomonas | aeroginosa | field isolate | FMV | Atypical growth |
| 23 | Pseudomonas | putida | field isolate | Maxivet inc. | No growth |
| 24 | Rhodococcus | equi | ATCC 6939 | FMV | No growth |
| 25 | Leuconostoc | mesenteroides | ATCC 8086 | ARS | No growth |
| 26 | Serratia | spp. | Field isolate | Maxivet inc. | No growth |
| 27 | Serratia | liquefaciens | Field isolate | SGSC | Atypical growth |
| 28 | Shigella | sonnei | ATCC 29930 | FMV | Atypical growth |
| 29 | Staphylococcus | aureus | ATCC 25923 | FMV | No growth |
| 30 | Yersinia | enterocolitica | Field isolate | FMV | No growth |
| 31 | Aeromonas | hydrophila | ATCC 7966 | SGSC | Atypical growth |

[a]FMV: Laboratory of Bacteriology, Diagnostic Service, Faculty of Veterinary Medicine, University of Montreal, Canada. SGSC: *Salmonella* Genetic Stock Center, Department of Biological Sciences, University of Calgary, Canada. ARS: Agricultural Research Service, Washington DC, 20250, USA.

4. Sample preparation: All the different foods were purchased from retail outlets near the locations where the experiments were conducted.

5. Food testing: The matrix study (using 5 types of food) was performed to evaluate the ability of the *Salmonella* and STEC strains recovery from the Actero *Salmonella*/STEC broth in comparison to the standard enrichment. Different enrichment conditions were used according to the type of food tested. The foods have been chosen for two reasons: 1) for the frequent implication in outbreaks of relevant forms of food poisoning or contamination, and 2) in function of the stress type supported by the target strain (cold and heat stress).

Methodology:

Whole Liquid Eggs:

Sample preparation: *S. enteritidis* (isolated from chicken wings) was streaked on TSBA and incubated overnight at 35° C. A few colonies were transferred to 9 mL of TSB for 6-7 hours at 35° C. The culture was diluted 1:10 in fresh TSB and was incubated overnight at the same temperature. Prior to inoculation, 1.5 mL of culture was heat-treated 2 minutes at 55° C. in a water bath to achieve a 50-80% injury of the inoculum. The degree of injury was determined by comparing the growth on selective and non-selective agar plates. The degree of injury obtained for the inoculum was 63%. Five thousand five hundred mL of whole liquid eggs was inoculated with at a level to yield fractionally positives results (1 CFU/100 g) and homogenized by shaking by hand. One thousand and five hundred mL of whole liquid eggs was left uninoculated. The two parts were stored at 4° C. for 48 h to allow the bacteria to stabilize in the food. An MPN (most probable number) analysis was prepared to estimate the level of contamination after the stabilization period. The inoculated part was divided in two set of twenty 100 g samples and the uninoculated part was divided in ten 100 g samples in filter-equipped stomacher bag.

Actero*Salmonella*/STEC enrichment: One set (20 inoculated and 5 uninoculated samples) was stomached 30 seconds with 300 mL of prewarmed Actero *Salmonella*/STEC broth and incubated at 39±0.5° C. for 7 h in a water bath. The samples were then streaked directly on Brilliant green sulfa agar (BGS) and on Xylose lysine Tergitol 4 agar (XLT4) and all presumptive colonies were confirmed by biochemical and serological procedure according to USDA/FSIS reference protocol for *Salmonella*.

Actero*Salmonella*/STEC enrichment confirmation: From the enriched Actero *Salmonella*/STEC sample, 0.5 ml were transferred into 10 mL Tetrathionate (Hajna) Broth and 0.1 ml into 10 mL modified Rappaport-Vassiliadis Soya broth (RVS) and were incubated at 42±0.5° C. for 22-24 h. They were then streaked to BGS and XLT4 and incubated at 35° C. for 18-24 h. If colonies were small or not visible, they were reincubated for an additional 18-24 h. Up to 3 typical colonies were picked per plate and transferred to TSI and LIA slants. Biochemical and serological procedures as in MLG 4.05 were performed to confirm positive samples.

Reference method enrichment: The second set (20 inoculated and 5 uninoculated samples) was enriched in 900 mL of buffered peptone water for 18-24 h at 35±2.0° C. and then processed according to USDA/FSIS reference protocol for *Salmonella*. The MPN samples were treated the same way. All presumed-positive samples were submitted to biochemical and serological identification recommended by the USDA/FSIS.

Raw Frozen Scallops:

Sample preparation: *S. saintpaul* was streaked on Blood Agar and incubated overnight at 35° C. A few colonies were transferred to 9 mL of TSB for 6-7 hours at 35° C. The culture was diluted 1:10 in fresh TSB and was incubated overnight at the same temperature. One thousand seventy hundred grams (1700 g) of raw frozen scallops was inoculated at a level to yield fractionally positives results (1.25 CFU/25 g) and homogenized by shaking by hands. Three hundred grams (300 g) of raw frozen scallops has been left uninoculated. The two parts were stored two weeks at minus 20° C. to permit the bacteria to stabilize in the food. An MPN (most probable number) analysis was prepared to estimate the level of contamination after the stabilization period. The inoculated part was divided in two sets of twenty 25 g samples and the uninoculated part was divided in two sets of 5 25 g samples.

Actero*Salmonella*/STEC enrichment: One set (20 inoculated and 5 uninoculated samples) was stomached 30 seconds with 50 mL of prewarmed Actero *Salmonella*/STEC broth and incubated at 39±0.5° C. for 7 h in a water bath. The samples were then streaked directly on Xylose lysine deoxycholate agar (XLD) and on Hektoen Enteric agar (HE) and all presumptive colonies were confirmed by biochemical and serological procedure according to BAM 5 reference protocol for *Salmonella*.

Actero*Salmonella*/STEC enrichment confirmation: From the enriched Actero *Salmonella*/STEC sample, 1.0 ml were transferred into 10 mL Tetrathionate Broth and 0.1 ml into 10 mL Rappaport-Vassiliadis broth (RV) and were incubated respectively at 35±2° C. and 42±0.5° C. for 22-24 h. They were then streaked on selective agar plate as in Bam 5 and presumptive positives were confirmed by biochemical and serological procedures according to the BAM 5 reference protocol for *Salmonella*.

Reference method enrichment: The second set of samples (20 inoculated and 5 uninoculated) were enriched in 225 mL of lactose broth, which was incubated at 35±2° C. for 24±2 h and was processed as in BAM 5 reference method for *Salmonella*. All presumed-positive samples were submitted to biochemical and serological identification as recommended by the FDA.

Raw Ground Chicken:

Sample preparation: Raw ground chicken naturally contaminated was used. To achieve fractional (low level) positive results, naturally contaminated ground chicken was carefully mixed with uncontaminated product to assure homogeneity (one thousand three hundred grams (1300 g) were prepared). For the high level portion, two hundred fifty grams (250 g) of the naturally contaminated ground chicken was left undiluted. An MPN analysis was set up to determine the level of *Salmonella* in the ground chicken. A low level contaminated part was divided into two sets of twenty 25 g samples and the high level contaminated part into ten 25 g samples. All the samples were placed in filter-equipped stomacher bag. Actero*Salmonella*/STEC enrichment: One set (20 low level and 5 high level samples) was stomached 30 seconds with 50 mL of prewarmed Actero *Salmonella*/STEC broth and incubated at 39±0.5° C. for 20 h in an incubator. They were then streaked to BGS and XLT4 and incubated at 35° C. for 18-24 h and all presumptive positive colonies were confirmed by biochemical and serological procedure according to USDA/FSIS reference protocol for *Salmonella*.

Actero*Salmonella*/STEC enrichment confirmation: From the enriched Actero *Salmonella*/STEC sample, 0.5 ml were transferred into 10 mL Tetrathionate (Hajna) Broth and 0.1 ml into 10 mL modified Rappaport-Vassiliadis Soya broth (RVS) and were incubated at 42±0.5° C. for 22-24 h. They were then streaked to BGS and XLT4 and incubated at 35° C. for 18-24 h. If colonies were small or not visible, they were reincubated for an additional 18-24 h. Up to 3 typical colonies were picked per plate and transferred to TSI and LIA slants. Biochemical and serological procedures as in MLG 4.05 were performed to confirm positive samples.

Reference method enrichment: The second set of samples (20 inoculated and 5 uninoculated samples) was enriched in 900 mL of buffered peptone water for 18-24 h at 35±2.0° C. and then processed according to USDA/FSIS reference protocol for *Salmonella*. The MPN samples were treated the same way. All presumed-positive samples were submitted to biochemical and serological identification as recommended by the USDA/FSIS.

Sprouts:

Sample preparation: *S. montevideo* was streaked on Blood Agar and incubated overnight at 35° C. A few colonies were transferred to 9 mL of TSB for 6-7 hours at 35° C. The culture was diluted 1:10 in fresh TSB and was incubated overnight at the same temperature. One thousand five hundred grams (1500 g) of sprouts was inoculated at a level to yield fractionally positives results (1.0 CFU/25 g) and carefully homogenized by shaking by hands. Four hundred grams (400 g) of sprouts has been left uninoculated. The two parts were stored at 4° C. for 48 h to allow the bacteria to stabilize in the food. An MPN analysis was prepared to estimate the level of contamination after the stabilization period. The inoculated part was divided in two set of twenty 25 g samples and the uninoculated part was divided in two set of five 25 g samples.

Actero*Salmonella*/STEC enrichment: One set (20 inoculated and 5 uninoculated samples) was stomached 30 seconds with 150 mL of prewarmed Actero *Salmonella*/STEC broth and incubated at 39±0.5° C. for 7 h in a water bath. From the enriched Actero *Salmonella*/STEC sample, 1.0 ml were transferred into 10 mL Tetrathionate Broth and 0.1 ml into 10 mL Rappaport-Vassiliadis broth (RV) and were incubated respectively at 43±0.2° C. and 42±0.2° C. for 18 h (because sprouts are considered to have high microbial load). They were then streaked on selective agar plate as in Bam 5 and presumptive positives were confirmed by biochemical and serological procedures according to the BAM 5 reference protocol for *Salmonella*.

Actero*Salmonella*/STEC enrichment confirmation: For the confirmation, the double enrichment of the Actero *Salmonella*/STEC samples were put back to incubation for 6 more hours for a total of 24 h (as recommended by the FDA). They were then streaked on selective agar plate as in Bam 5 and presumptive positives were confirmed by biochemical and serological procedures according to the BAM 5 reference protocol for *Salmonella*.

Reference method enrichment: The second set of samples (20 inoculated and 5 uninoculated) were enriched in 225 mL of lactose broth, which was incubated at 35±2° C. for 24±2 h and was processed as in BAM 5 reference method for *Salmonella*. All presumed-positive samples were submitted to biochemical and serological identification recommended by the FDA.

Results: All the results from the comparison method study are summarized in tables 10, 11 [In whole liquid eggs, using the Actero *Salmonella*/STEC broth for an enrichment of 7 h in a water bath at 39° C., 10 samples out of 20 were detected positives. A double enrichment of the Actero *Salmonella*/STEC enriched samples according to the USDA/FSIS reference protocol confirmed the results for specificity of 100%

(Table 10). From the 20 samples tested by the reference method, 10 were confirmed positives. The non-inoculated samples were all found negative by both the FoodChek Actero *Salmonella*/STEC enrichment method and the USDA/FSIS reference method (Table 11).

A) In raw frozen scallops, again, the performance of the FoodChek enrichment method using the Actero *Salmonella*/STEC broth was similar to the reference method. Effectively, using the Actero *Salmonella*/STEC broth for an enrichment of 7 hr in a water bath, 5 samples were confirmed positives from the 20 inoculated at the fractional level for a specificity of 100% (Table 10). The FDA (BAM 5) reference method detected 4 positives samples. All the non-inoculated samples were confirmed negatives by both methods. The statistical analysis (unpaired study) of the results obtained shows that there is not a significant difference between the FoodChek Actero *Salmonella*/STEC enrichment methods and USDA/FSIS reference method (Table 11).

B) In raw ground chicken, naturally contaminated samples were tested. The FoodChek Actero*Salmonella*/STEC method, consisting of an enrichment of 20 h at 39° C. in an incubator using the Actero *Salmonella*/STEC broth, detected 7 positives from the 20 analysed. The confirmation by double enrichment of the samples enriched in Actero *Salmonella*/STEC also yields the same 7 positives for a specificity of 100% (Table 10). The reference method detected 10 positives samples from the 20 tested. Both methods detected the 5 high level samples naturally contaminated. As it is an unpaired study, the statistical analysis of the results obtained shows that there is not a significant difference between the FoodChek Actero *Salmonella*/STEC enrichment methods and USDA/FSIS reference method (Table 11).

C) In sprouts, the FoodChek enrichment method consisting of a first enrichment in a water bath for 7 h at 39° C. in the Actero *Salmonella*/STEC broth and a second enrichment in TT broth and RV for 18 h in water baths at 43° C. and 42° C. respectively found 11 confirmed positives samples from the 20 prepared (Table 10). For the reference method, unfortunately, very few typical colonies were isolated and they were all negative by biochemical testing. There was up to three attempts to reisolate the non-isolated typical colonies, but none of them were found positive for *Salmonella* by biochemical testing. The only positive result found is a 50 g sample from the MPN analysis. The statistical analysis of the results obtained here shows that there is as significant difference between both methods (Table 11).

TABLE 10

FoodChek Actero *Salmonella*/STEC Method Presumptive vs. Confirmed

| Matrix | Strain | MPN[a]/ test portion | N[c] | x[d] | FoodChek Actero *Salmonella*/STEC Method Presumptive | | | FoodChek Actero *Salmonella*/STEC Method Confirmed | | | | |
|---|---|---|---|---|---|---|---|---|---|---|---|---|
| | | | | | POD$_{CP}$[e] | 95% CI | x | POD$_{CC}$[f] | 95% CI | dPOD$_{CP}$[g] | 95% CI[h] |
| Whole liquid eggs | S. enteritidis | 0 | 5 | 0 | 0 | (0.00, 0.43) | 0 | 0 | (0.00, 0.43) | 0 | (−0.43, 0.43) |
| | | 0.67 | 20 | 10 | 0.5 | (0.30, 0.70) | 10 | 0.5 | (0.30, 0.70) | 0 | (−0.28, 0.28) |
| Raw frozen scallops | S. saintpaul | 0 | 5 | 0 | 0 | (0.00, 0.43) | 0 | 0 | (0.00, 0.43) | 0 | (−0.43, 0.43) |
| | | 0.17 | 20 | 5 | 0.25 | (0.11, 0.47) | 5 | 0.25 | (0.11, 0.47) | 0 | (−0.26, 0.26) |
| Raw ground chicken | Naturally contaminated | 1150 | 5 | 5 | 1 | (0.57, 1.00) | 5 | 1 | (0.57, 1.00) | 0 | (−0.43, 0.43) |
| | | 0.67 | 20 | 7 | 0.35 | (0.18, 0.57) | 7 | 0.35 | (0.18, 0.57) | 0 | (−0.28, 0.28) |
| Sprouts | S. montevideo | 0 | 5 | 0 | 0 | (0.00, 0.43) | 0 | 0 | (0.00, 0.43) | 0 | (−0.43, 0.43) |
| | | N/A | 20 | 11 | 0.55 | (0.34, 0.74) | 11 | 0.55 | (0.34, 0.74) | 0 | (−0.28, 0.28) |

[a] MPN = Most Probable Number is based on the POD of reference method test portions across labs using the AOAC MPN calculator, with 95% confidence interval
[b] N/A = Not applicable
[c] N = Number of test potions
[d] x = Number of positive test portions
[e] POD$_{CP}$ = Candidate method presumptive positive outcomes divided by the total number of trials
[f] POD$_{CC}$ = Candidate method confirmed positive outcomes divided by the total number of trials
[g] dPOD$_{CP}$ = Difference between the candidate method presumptive result and candidate method confirmed result POD values
[h] 95% CI = If the confidence interval of a dPOP does not contain zero, then the difference is statistically significant at the 5% level

TABLE 11

Method Comparison Results

| Matrix | Strain | MPN[a]/ test portion | N[c] | x[d] | FoodChek Actero *Salmonella*/STEC Method | | | Reference Method | | | | |
|---|---|---|---|---|---|---|---|---|---|---|---|---|
| | | | | | POD$_C$[e] | 95% CI | x | POD$_R$[f] | 95% CI | dPOD$_C$[g] | 95% CI[h] |
| Whole liquid eggs | S. enteritidis | 0 | 5 | 0 | 0 | (0.00, 0.43) | 0 | 0 | (0.00, 0.43) | 0 | (−0.43, 0.43) |
| | | 0.67 | 20 | 10 | 0.5 | (0.30, 0.70) | 10 | 0.5 | (0.30, 0.70) | 0 | (−0.28, 0.28) |
| Raw frozen scallops | S. saintpaul | 0 | 5 | 0 | 0 | (0.00, 0.43) | 0 | 0 | (0.00, 0.43) | 0 | (−0.43, 0.43) |
| | | 0.17 | 20 | 5 | 0.25 | (0.11, 0.47) | 4 | 0.2 | (0.08, 0.42) | 0.05 | (−0.21, 0.30) |
| Raw ground chicken | Naturally contaminated | 1150 | 5 | 5 | 1 | (0.57, 1.00) | 5 | 1 | (0.57, 1.00) | 0 | (−0.43, 0.43) |
| | | 0.67 | 20 | 7 | 0.35 | (0.18, 0.57) | 10 | 0.5 | (0.30, 0.70) | −0.15 | (−0.41, 0.15) |

TABLE 11-continued

Method Comparison Results

| Matrix | Strain | MPN[a]/test portion | N[c] | x[d] | POD$_C$[e] | 95% CI | x | POD$_R$[f] | 95% CI | dPOD$_C$[g] | 95% CI[h] |
|---|---|---|---|---|---|---|---|---|---|---|---|
| Sprouts | S. montevideo | 0 | 5 | 0 | 0 | (0.00, 0.43) | 0 | 0 | (0.00, 0.43) | 0 | (−0.43, 0.43) |
|  |  | N/A | 20 | 11 | 0.55 | (0.34, 0.74) | 0 | 0 | (0.00, 0.16) | 0.55 | (0.29, 0.74) |

[a]MPN = Most Probable Number is based on the POD of reference method test portions across labs using the AOAC MPN calculator, with 95% confidence interval
[b]N/A = Not applicable
[c]N = Number of test potions
[d]x = Number of positive test portions
[e]POD$_C$ = Confirmed candidate method positive outcomes divided by the total number of trials
[f]POD$_R$ = Confirmed reference method positive outcomes divided by the total number of trials
[g]dPOD$_C$ Difference between the candidate method and reference method POD values
[h]95% CI = If the confidence interval of a dPOD does not contain zero, then the difference is statistically significant at the 5% level The embodiments and examples presented herein are illustrative of the general nature of the subject matter claimed and are not limiting. It will be understood by those skilled in the art how these embodiments can be readily modified and/or adapted for various applications and in various ways without departing from the scope of the subject matter claimed. The claims hereof are to be understood to include without limitation all alternative embodiments and equivalents of the subject matter hereof. Phrases, words and terms employed herein are illustrative and are not limiting. Where permissible by law, all references cited herein are incorporated herein by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed. Particular embodiments may alternatively comprise or consist of or exclude any one or more of the elements disclosed.

The embodiments of the invention in which an exclusive property or privilege is claimed are defined as follows:

1. A culture medium comprising
   a biologically effective concentration of a nutrient mixture;
   calcium chloride;
   potassium phosphate;
   magnesium sulfate;
   sodium chloride;
   sodium phosphate;
   citric acid;
   vitamin B12 at a concentration of about 0.0001 to about 0.001 g/L;
   ethanolamine at a concentration of about 1.0 to about 3.0 g/L;
   ferrous sulfate at a concentration of about 0.01 to about 0.05 g/L; and
   sodium pyruvate at a concentration of about 0.5 to about 2.0 g/L.

2. The medium according to claim 1 wherein the nutrient mixture comprises yeast extract.

3. The medium according to claim 2 wherein the yeast extract is present at a concentration of about 1 to about 4 g/L.

4. The medium according to claim 3 wherein vitamin B12 is present at a concentration of about 0.0005 g/L; ethanolamine is present at a concentration of about 2.0 g/L; ferrous sulfate is present at a concentration of about 0.019 g/L; and sodium pyruvate is present at a concentration of about 1.0 g/L.

5. A method for culturing bacteria in a biological sample, the method comprising the step of incubating the sample in the medium of claim 1.

6. The method according to claim 5 wherein the medium comprises yeast extract at a concentration of about 1 to about 4 g/L.

7. The method according to claim 6 wherein the medium comprises vitamin B12 at a concentration of about 0.0005 g/L; ethanolamine at a concentration of about 2.0 g/L; ferrous sulfate at a concentration of about 0.019 g/L; and sodium pyruvate at a concentration of about 1.0 g/L.

8. The method according to claim 5 wherein the bacteria are Salmonella or Escherichia coli.

9. The method according to claim 8 wherein the Escherichia coli are E. coli O157, shiga toxin-producing Escherichia coli (STEC), enteropathogenic E. coli (EPEC), enterohemorrhagic E. coli (EHEC), enterotoxigenic E. coli (ETEC), enteroinvasive E. coli (EIEC) or enteroaggregative E. coli (EAEC).

10. The method according to claim 5, further comprising a step of detecting Salmonella or Escherichia coli after the incubating step.

11. The method according to claim 10 wherein the detecting step comprises a polymerase chain reaction (PCR), lectin binding, simple diffusion, lateral diffusion, antibody binding, lateral flow, immunological detection, ELISA or flow through step.

* * * * *